(12) United States Patent
Ishii et al.

(10) Patent No.: US 8,187,891 B2
(45) Date of Patent: May 29, 2012

(54) METHODS FOR DETECTION AND DETERMINATION OF VITAMIN C BY LUMINESCENCE

(75) Inventors: Kazuyuki Ishii, Tokyo (JP); Kensuke Kubo, Tokyo (JP); Kikuo Komori, Tokyo (JP); Yasuyuki Sakai, Tokyo (JP)

(73) Assignee: The University of Tokyo, Tokyo (JP)

( * ) Notice: Subject to any disclaimer, the term of this patent is extended or adjusted under 35 U.S.C. 154(b) by 142 days.

(21) Appl. No.: 12/726,294

(22) Filed: Mar. 17, 2010

(65) Prior Publication Data

US 2010/0239506 A1 Sep. 23, 2010

(30) Foreign Application Priority Data

Mar. 17, 2009 (JP) ................................. 2009-063951
Feb. 23, 2010 (JP) ................................. 2010-037544

(51) Int. Cl.
*G01N 33/00* (2006.01)
*G01N 21/64* (2006.01)

(52) U.S. Cl. ............ 436/93; 436/63; 436/127; 436/128; 436/131; 436/166; 436/172

(58) Field of Classification Search ............... 436/63, 436/93, 127–128, 131, 166, 172
See application file for complete search history.

(56) References Cited

U.S. PATENT DOCUMENTS

| | | | | |
|---|---|---|---|---|
| 4,803,161 A | * | 2/1989 | Babb et al. | 435/29 |
| 4,863,717 A | * | 9/1989 | Keana | 424/9.321 |
| 5,037,762 A | * | 8/1991 | Mura et al. | 436/164 |
| 5,045,477 A | * | 9/1991 | Belly et al. | 436/164 |
| 5,089,181 A | * | 2/1992 | Hauser | 424/1.21 |
| 5,169,637 A | * | 12/1992 | Lenk et al. | 424/450 |
| 6,153,399 A | | 11/2000 | Fujishiro et al. | |
| 2003/0068275 A1 | * | 4/2003 | Lippard et al. | 424/9.36 |

FOREIGN PATENT DOCUMENTS

JP 11-326207 A 11/1999
JP 4073963 B2 4/2008

OTHER PUBLICATIONS

Paleos, C. M. et al, Journal of the Chemical Society, Chemical Communications 1977, 345-346.*
Blough, N. V. et al, Journal of the American Chemical Society 1988, 110, 1915-1917.*
Green, S. A. et al, Journal of the American Chemical Society 1990, 112, 7337-7346.*
Yang, X.-F. et al, Analyst 2001, 126, 1800-1804.*
Aliaga, C. et al, Organic Letters 2003, 5, 4145-4148.*
Likhtenstein, G. I. et al, Photochemistry and Photobiology 2007, 83, 871-881.*

(Continued)

*Primary Examiner* — Arlen Soderquist
(74) *Attorney, Agent, or Firm* — Osha • Liang LLP

(57) ABSTRACT

The present invention provides a method for detection or determination of vitamin C by luminescence that employs a redox-responsive fluorogenic probe consisting of porphyrin or phthalocyanine with a nitroxide radical(s), or that employs a liposome preparation comprising the said redox-responsive fluorogenic probe. The present method can overcome the problems of prior art methods, and in particular, are applicable for bioimaging to allow elucidation of the behavior of vitamin C in vivo.

20 Claims, 6 Drawing Sheets

OTHER PUBLICATIONS

Qi Chen et al., "Pharmacologic ascorbic acid concentrations selectively kill cancer cells: Action as a pro-drug to deliver hydrogen peroxide to tissues" Proc. Natl. Acad. Sci. USA, Vplume 102, No. 38, pp. 13604-13609 (2005) (6 pages).

E. Lozinsky et al., "Dual fluorophore-nitroxide probes for analysis of vitamin C in biological liquids"; Journal of Biochemical and Biophysical Methods 38, pp. 29-42 (1999) (14 pages).

K. Ishii et al., "The Photophysical Properties of Phthalocyanines and Related Compounds"; The Porphirin Handbook; ed by K. Kadish, K.M. Smith and R. Guilard, Academic Press, vol. 16, pp. 1-42 (2003) (42 pages).

H. Miwa, K. Ishii et al., "Electronic Structures of Zinc and Palladium Tetraazaporphyrin Derivatives Controlled by Fused Benzo Rings" Chemistry A European Journal, pp. 4422-4435 (2004) (15 pages).

K. Ishii et al., "Relationship between Symmetry of Porphyrinic π-Conjugated Systems and Singlet Oxygen ($1\Delta g$) Yields: Low-Symmetry Teraazaporphyrin Derivatives" J. Phys. Chem. A 109, pp. 5781-5787 (2005) (7 pages).

K. Ishii et al., "Electronic Absorption, MCD and Fluorescence Studies on Phthalocyaninatosilicon Covalently Linked to One or Two TEMPO Radicals" Journal of Porphyrins and Phthalocyanines 3, pp. 439-443 (1999) (10 pages).

K. Ishii et al.; "Time Resolved EPR, Fluorescence, and Transient Absorption Studies on Phthalocyaninatosilicon Covalently Linked to One or Two TEMPO Radicals"; Journal of the American Chemical Society vol. 123, No. 4, pp. 702-708 (2001) (8 pages).

K. Ishii et al., "Relationship between Electron Spin Polarization, Electron Exchange Interaction, and Lifetime: The Excited Multiplet States of Phthalocyaninatosilicon Covalently Linked to One Nitroxide Radical"; The Journal of Physical Chemistry A, vol. 105 No. 28, pp. 6794-6799 (2001) (7 pages).

K. Ishii et al., "Time-Resolved EPR and Transient Absorption Studies on Phthalocyaninatosilicon Covalently Linked to Two PROXYL Radicals"; The Journal of Physical Chemistry A, vol. 108, No. 16, pp. 3276-3280 (2004) (6 pages).

K. Ishii et al., "In vitro photodynamic effects of phthalocyaninatosilicon covalently linked to 2,2,6,6-tetramethyl-1-piperidinyloxy radicals on cancer cells" Free Radical Biology & Medicine 38, pp. 920-927 (2005) (8 pages).

K. Ishii et al., "Efficient Singlet Oxygen Generation without Heavy-atom Effect" Seisan Kenkyu vol. 60(2), pp. 160-163 (2008) (5 pages).

Yang Liu et al., "TEMPO-based Redox-sensitive Fluorescent Probes and Their Applications to Evaluating Intracellular Redox Status in Living Cells" Chemistry Letters vol. 38, No. 6, pp. 588-589 (2009) (2 pages).

\* cited by examiner

R1                    R2

(A)    (B)

(A)

(B)

METHODS FOR DETECTION AND DETERMINATION OF VITAMIN C BY LUMINESCENCE

CROSS REFERENCE TO RELATED APPLICATIONS

This Application claims priorities of Japanese Patent Application No. 2009-063951, filed on Mar. 17, 2009 and Japanese Patent Application No. 2010-037544, filed on Feb. 23, 2010, the entirety of which is incorporated by reference herein.

BACKGROUND OF THE INVENTION

1. Field of the Invention

The present invention relates to redox-responsive fluorogenic probes and liposome preparations comprising them, and to methods for detection and determination of vitamin C employing the same. Specifically, the present invention relates to a fluorogenic probe consisting of a porphyrin or phthalocyanine with a nitroxide radical(s), and especially a (phthalocyaninato)silicon complex with a nitroxide radical(s) as an axial ligand(s), to a liposome preparation comprising it, and to in vivo and in vitro methods for detection and determination of vitamin C using the same.

2. Description of Related Art

It is well known that vitamin C (ascorbic acid) is a water-soluble vitamin that is widely distributed in the plant kingdom, being particularly abundant in fruits and in green and yellow vegetables. Vitamin C plays important roles in body functions including (1) amino acid biosynthesis, (2) hormone secretion from the adrenal gland, and (3) synthesis of L-carnitine, a carrier that transports fatty acids to the mitochondria. It is also necessary for production of collagen in the connective tissue, and vitamin C deficiency is manifested as scurvy symptoms (loose teeth, weakening of blood vessels, hemorrhaging from the skin, impaired wound recovery and immunological function and mild anemia).

Because humans cannot synthesize vitamin C in the body, they must take in their entire required amount from the external environment through food, for example. Vitamin C is also known to have powerful antioxidant activity. Therefore, it is often added to processed foods and health foods as an antioxidant vitamin or as an antioxidant food additive.

The HPLC method, hydrazine colorimetric method and indophenol method have been used in the prior art as methods for detecting and determining vitamin C in foods or biological samples. Other methods have also been reported, such as a method involving two reactions conducted in the same reaction system, namely a reaction in which reduced ascorbic acid and oxygen yield oxidized ascorbic acid and hydrogen peroxide in the presence of ascorbate oxidase and a reaction in which the generated hydrogen peroxide and a chromogen are reacted in the presence of a peroxidase to produce pigments, and the ascorbic acid in the sample is determined based on the produced pigments (see Japanese Patent No. 4073963, for example), or a method wherein o-phenylenediamine is added to a vitamin C-containing sample and the sample is irradiated with polarized excitation light, the degree of polarization of the produced fluorescence is measured, and the quantity of vitamin C is determined based on the measured value (see Japanese Unexamined Patent Publication No. H11-326207, for example). These determination methods, however, still have problems such as complicated procedures (including those for pretreatment), needs of long periods for quantification, and/or low precision.

In recent years, the link between vitamin C and aging has been a focus of attention while high dosage treatment of vitamin C has also been reported to be effective for treatment of cancer. For example, an article on cancer treatment published in 2005, entitled "Pharmacologic ascorbic acid concentrations selectively kill cancer cells" has received interest, and results have been reported indicating that drip infusion of high concentration vitamin C is effective for cancer treatment (see Qi chen et al., Proc. Natl. Acad. Sci. USA 102 (38), 13604-13609 (2005), for example). However, the precise behavior of vitamin C in vivo has not been fully elucidated, and bioimaging and related technologies are highly expected to shed light on its in vivo function. Yet none of the methods mentioned above can be applied for bioimaging of vitamin C.

Methods applicable to bioimaging would be detection and determination of vitamin C by luminescence, such as a method using a dual molecule comprising a fluorescent chromophoric group such as dansyl or pyryl and a nitroxide radical, as a fluorogenic probe (see E. Lozinsky et al., J. Biochem. Biophys. Methods 38, 29-42 (1999), for example). Such fluorogenic probes, however, have a wavelength range of low permeability to biological tissue ($\leqq 650$ nm) for both their excitation light and fluorescence, and are therefore poorly applicable for fluorescent bioimaging.

BRIEF SUMMARY OF THE INVENTION

Problems to be Solved by the Invention

We have previously reported on the photophysical properties of porphyrins or phthalocyanines (see K. Ishii et al., The Porphirin Handbook; ed by K. Kadish, K. M. Smith and R. Guilard, Academic Press, Volume 16, 1-42 (2003); H. Miwa, K. Ishii et al., Chem. Eur. J. 10, 4422-4435 (2004); and K. Ishii et al., J. Phys. Chem. A 109 (26), 5781-5787 (2005), for example). It was shown that nitroxide radicals have a powerful quenching function on phthalocyanine fluorescence (see K. Ishii et al., J. Porphyrins Phthalocyanines 3, 439-443 (1999); K. Ishii et al., J. Am. Chem. Soc. 123 (4), 702-708 (2001); K. Ishii et al., J. Phys. Chem. A 105 (28), 6794-6799 (2001); and K. Ishii et al., J. Phys. Chem. A 108 (16), 3276-3280 (2004), for example). Nitroxide radicals are known to react with vitamin C (and a few other reactive substances) and lose their unpaired electrons (lose their radical nature). We focused on these facts, and completed the present invention as a result of considering and studying the idea that vitamin C concentration might be quantifiable and detectable from the increase in luminescence intensity by reaction with vitamin C.

It is an object of the present invention to provide novel methods for detection and determination of vitamin C that can overcome the problems of the prior art, and particularly methods for detection and determination of vitamin C by luminescence that are applicable for bioimaging to allow elucidation of the behavior of vitamin C in vivo (e.g. in cells) for research purposes. It is another object of the present invention to provide useful fluorogenic probes for the methods.

Means for Solving the Problems

Specifically, as described below, the present invention provides a method for detection or determination of vitamin C by luminescence that employs a redox-responsive fluorogenic probe consisting of porphyrin or phthalocyanine with a nitroxide radical(s), or that employs a liposome preparation comprising the said redox-responsive fluorogenic probe.

1. A method for detection or determination of vitamin C in a sample, the method comprising the following steps:
(1) contacting a redox-responsive fluorogenic probe consisting of a porphyrin or a phthalocyanine with a nitroxide radical(s) under irradiation with excitation light, with a sample;
(2) monitoring the luminescence; and
(3) optionally, determining the concentration of vitamin C in the sample based on the time-profile of luminescence intensity.

2. The method according to claim 1, wherein the porphyrin or the phthalocyanine with a nitroxide radical(s) is a compound of the following formula I:

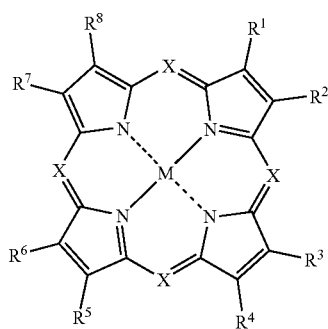

wherein

X is N or CR', where R' is a hydrogen atom, a $C_{1-18}$ alkyl group, an aryl group or a nitrogen-containing heterocyclyl group;

M is $H_2$ or an atom selected from elements of Groups 2-4 or Groups 8-15 of the Periodic Table;

when M is an atom selected from elements of Groups 2-4 or Groups 8-15 of the Periodic Table, 1 or 2 axial ligands L may be present, where each L is independently a halogen atom, a hydroxyl group, a tri($C_{1-18}$ alkyl)silyloxy group or a nitroxide radical;

$R^1$, $R^2$, $R^3$, $R^4$, $R^5$, $R^6$, $R^7$ and $R^8$ are, independently of one another, a hydrogen atom, a $C_{1-18}$ alkyl group, a $C_{1-18}$ alkoxy group, an aryl group, a nitrogen-containing heterocyclyl group or a nitroxide radical, or $R^1$ and $R^2$ form an aromatic ring or a nitrogen-containing hetero ring together with the carbon atoms to which they are bonded, and the aromatic ring or the nitrogen-containing hetero ring is unsubstituted or substituted with one or more substituents selected from the group consisting of a halogen atom, a hydroxyl group, a sulfo group, a carboxyl group, a $C_{1-18}$ alkyl group, a $C_{1-18}$ alkoxy group, —$S(O)_{0-2}$—$C_{1-18}$ alkyl, —$(OCH_2CH_2)_{1-8}$—O—$C_{1-6}$ alkyl, an aryl group and a nitrogen-containing heterocyclyl group, or may form a ring containing a nitroxide radical(s) together with two adjacent ring atoms of the aromatic ring or the nitrogen-containing hetero ring, $R^3$ and $R^4$ form an aromatic ring or nitrogen-containing hetero ring together with the carbon atoms to which they are bonded, and the aromatic ring or the nitrogen-containing hetero ring is unsubstituted or substituted with one or more substituents selected from the group consisting of a halogen atom, a hydroxyl group, a sulfo group, a carboxyl group, a $C_{1-18}$ alkyl group, a $C_{1-18}$ alkoxy group, —$S(O)_{0-2}$—$C_{1-18}$ alkyl, —$(OCH_2CH_2)_{1-8}$—O—$C_{1-6}$ alkyl, an aryl group and a nitrogen-containing heterocyclyl group, or may form a ring containing a nitroxide radical(s) together with two adjacent ring atoms of the aromatic ring or the nitrogen-containing hetero ring, $R^5$ and $R^6$ form an aromatic ring or nitrogen-containing hetero ring together with the carbon atoms to which they are bonded, and the aromatic ring or the nitrogen-containing hetero ring is unsubstituted or substituted with one or more substituents selected from the group consisting of a halogen atom, a hydroxyl group, a sulfo group, a carboxyl group, a $C_{1-18}$ alkyl group, a $C_{1-18}$ alkoxy group, —$S(O)_{0-2}$—$C_{1-18}$ alkyl, —$(OCH_2CH_2)_{1-8}$—O—$C_{1-6}$ alkyl, an aryl group and a nitrogen-containing heterocyclyl group, or may form a ring containing a nitroxide radical(s) together with two adjacent ring atoms of the aromatic ring or the nitrogen-containing hetero ring, or $R^7$ and $R^8$ form an aromatic ring or nitrogen-containing hetero ring together with the carbon atoms to which they are bonded, and the aromatic ring or the nitrogen-containing hetero ring is unsubstituted or substituted with one or more substituents selected from the group consisting of a halogen atom, a hydroxyl group, a sulfo group, a carboxyl group, a $C_{1-18}$ alkyl group, a $C_{1-18}$ alkoxy group, —$S(O)_{0-2}$—$C_{1-18}$ alkyl, —$(OCH_2CH_2)_{1-8}$—O—$C_{1-6}$ alkyl, an aryl group and a nitrogen-containing heterocyclyl group, or may form a ring containing a nitroxide radical(s) together with two adjacent ring atoms of the aromatic ring or the nitrogen-containing hetero ring; with the proviso that at least one nitroxide radical is present in the compound.

3. The method according to claim 1, wherein the porphyrin or the phthalocyanine with a nitroxide radical(s) is a compound of the following formula II:

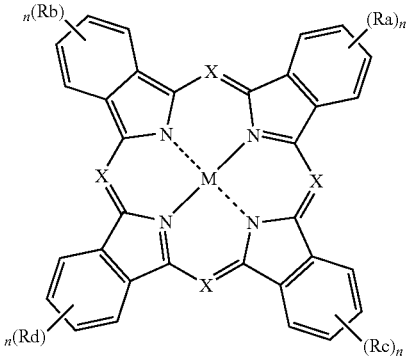

wherein

X is N or CR', where R' is a hydrogen atom, a $C_{1-18}$ alkyl group, an aryl group or a nitrogen-containing heterocyclyl group;

M is $H_2$ or an atom selected from elements of Groups 2-4 or Groups 8-15 of the Periodic Table;

when M is an atom selected from elements of Groups 2-4 or Groups 8-15 of the Periodic Table, 1 or 2 axial ligands L may be present, where each L is independently a halogen atom, a hydroxyl group, a tri($C_{1-18}$ alkyl)silyloxy group or a nitroxide radical;

each n is independently 0, 1, 2, 3 or 4; and

Ra, Rb, Rc and Rd are, independently of one another, a halogen atom, a hydroxyl group, a sulfo group, a carboxyl group, a $C_{1-18}$ alkyl group, a $C_{1-18}$ alkoxy group, —$S(O)_{0-2}$—$C_{1-18}$ alkyl, —$(OCH_2CH_2)_{1-8}$—O—$C_{1-6}$ alkyl, an aryl group or a nitrogen-containing heterocyclyl group, or when n is 2, two adjacent groups of each Ra, Rb, Rc and Rd may form a ring containing a nitroxide radical(s) together with ring atoms to which they are bonded;

with the proviso that at least one nitroxide radical is present in the compound.

4. The method according to claim 3, wherein M is an atom selected from elements of Group 2 or Groups 12-15 of the Periodic Table, and 1 or 2 axial ligands L are present.

5. The method according to claim 3, wherein the ring containing a nitroxide radical(s) formed together with ring atoms is 2,2,6,6-tetramethyl-1-piperidinyloxy (TEMPO) or 2,2,5,5-tetramethyl-1-pyrrolidinyloxy (PROXYL).

6. The method according to claim 1, wherein the porphyrin or the phthalocyanine with a nitroxide radical(s) is a complex of the following formula III:

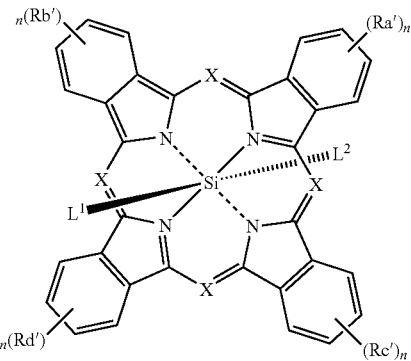

wherein

X is N or CR', where R' is a hydrogen atom, a $C_{1-18}$ alkyl group, an aryl group or a nitrogen-containing heterocyclyl group;

one of $L^1$ and $L^2$ is a nitroxide radical, and the other is a halogen atom, a hydroxyl group, a tri($C_{1-18}$ alkyl)silyloxy group or a nitroxide radical;

Ra', Rb', Rc' and Rd' are, independently of one another, a halogen atom, a hydroxyl group, a sulfo group, a carboxyl group, a $C_{1-18}$ alkyl group, a $C_{1-18}$ alkoxy group, —S(O)$_{0-2}$—$C_{1-18}$ alkyl, —(OCH$_2$CH$_2$)$_{1-8}$—O—$C_{1-6}$ alkyl, an aryl group or a nitrogen-containing heterocyclyl group; and each n is independently 0, 1, 2, 3 or 4.

7. The method according to claim 6, wherein X is N.

8. The method according to claim 6, wherein the nitroxide radical in $L^1$ or $L^2$ is of the following formula IV:

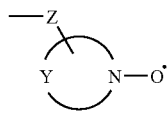

wherein

Y, together with N, forms a 5- to 6-membered, saturated or partially unsaturated, nitrogen-containing hetero ring, where the two atoms adjacent to the >N—O. group are tertiary carbon atoms, and the nitrogen-containing hetero ring optionally includes an additional N or O atom; and Z is a single bond or a spacer.

9. The method according to claim 8, wherein the nitroxide radical is a group comprising a 5- to 6-membered, saturated or partially unsaturated, nitrogen-containing hetero ring structure selected from 2,2,6,6-tetramethyl-1-piperidinyloxy (TEMPO), 2,2,5,5-tetramethyl-1-pyrrolidinyloxy (PROXYL), 4,4-dimethyl-3-oxazolidinyloxy (DOXYL) or nitronylnitroxide (NN).

10. The method according to claim 1, characterized in that the redox-responsive fluorogenic probe consisting of the porphyrin or the phthalocyanine with a nitroxide radical(s) is used in the form of a liposome preparation.

11. A method for detection of vitamin C in vivo, the method comprising the following steps:
(1) administering a redox-responsive fluorogenic probe consisting of a porphyrin or a phthalocyanine with a nitroxide radical(s) to a subject; and
(2) irradiating the subject with excitation light having a wavelength of 650 nm or greater, and monitoring the luminescence.

12. The method according to claim 11, characterized in that the redox-responsive fluorogenic probe consisting of the porphyrin or the phthalocyanine with a nitroxide radical(s) is used in the form of a liposome preparation.

13. The method according to claim 12, wherein the porphyrin or the phthalocyanine with a nitroxide radical(s) is a compound of the following formula I:

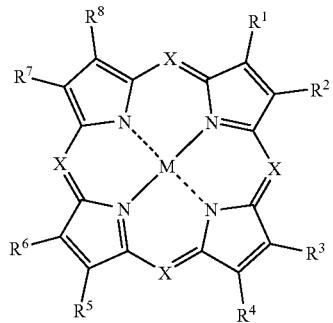

wherein

X is N or CR', where R' is a hydrogen atom, a $C_{1-18}$ alkyl group, an aryl group or a nitrogen-containing heterocyclyl group;

M is $H_2$ or an atom selected from elements of Groups 2-4 or Groups 8-15 of the Periodic Table;

when M is an atom selected from elements of Groups 2-4 or Groups 8-15 of the Periodic Table, 1 or 2 axial ligands L may be present, where each L is independently a halogen atom, a hydroxyl group, a tri($C_{1-18}$ alkyl)silyloxy group or a nitroxide radical;

$R^1$, $R^2$, $R^3$, $R^4$, $R^5$, $R^6$, $R^7$ and $R^8$ are, independently of one another, a hydrogen atom, a $C_{1-18}$ alkyl group, a $C_{1-18}$ alkoxy group, an aryl group, a nitrogen-containing heterocyclyl group or a nitroxide radical, or $R^1$ and $R^2$ form an aromatic ring or a nitrogen-containing hetero ring together with the carbon atoms to which they are bonded, and the aromatic ring or the nitrogen-containing hetero ring is unsubstituted or substituted with one or more substituents selected from the group consisting of a halogen atom, a hydroxyl group, a sulfo group, a carboxyl group, a $C_{1-18}$ alkyl group, a $C_{1-18}$ alkoxy group, —S(O)$_{0-2}$—$C_{1-18}$ alkyl, —(OCH$_2$CH$_2$)$_{1-8}$—O—$C_{1-6}$ alkyl, an aryl group and a nitrogen-containing heterocyclyl group, or may form a ring containing a nitroxide radical(s) together with two adjacent ring atoms of the aromatic ring or the nitrogen-containing hetero ring, $R^3$ and $R^4$ form an aromatic ring or nitrogen-containing hetero ring together with the carbon atoms to which they are bonded, and the aromatic ring or the nitrogen-containing hetero ring is unsubstituted or substituted with one or more substituents selected from the group consisting of a halogen atom, a hydroxyl group, a sulfo group, a carboxyl group, a $C_{1-18}$ alkyl group, a $C_{1-18}$ alkoxy group, —S(O)$_{0-2}$—$C_{1-18}$ alkyl, —(OCH$_2$CH$_2$)$_{1-8}$—O—$C_{1-6}$ alkyl, an aryl group and a nitrogen-containing heterocyclyl group, or may form a ring containing a nitroxide radical(s) together with two adjacent ring atoms of the aromatic ring or the nitrogen-containing hetero ring, $R^5$ and $R^6$ form an aromatic ring or nitrogen-containing hetero ring together with the carbon atoms to which they are bonded, and the aromatic ring or the nitrogen-containing hetero ring is unsubstituted or substituted with one or more substituents selected from the group consisting of a halogen atom, a hydroxyl group, a sulfo group, a carboxyl group, a $C_{1-18}$ alkyl group, a $C_{1-18}$ alkoxy group, —S(O)$_{0-2}$—$C_{1-18}$ alkyl, —(OCH$_2$CH$_2$)$_{1-8}$—O—$C_{1-6}$ alkyl, an aryl group and a nitrogen-containing heterocyclyl group, or may form a ring containing a nitroxide radical(s) together with two adjacent ring atoms of the aromatic ring or the nitrogen-containing hetero ring, or $R^7$ and $R^8$ form an aromatic ring or nitrogen-containing hetero ring together with the carbon atoms to which they are bonded, and the aromatic ring or the nitrogen-containing hetero ring is unsubstituted or substituted with one or more substituents selected from the group consisting of a halogen atom, a hydroxyl group, a sulfo group, a carboxyl group, a $C_{1-18}$ alkyl group, a $C_{1-18}$ alkoxy group, —S(O)$_{0-2}$—$C_{1-18}$ alkyl, —(OCH$_2$CH$_2$)$_{1-8}$—O—$C_{1-6}$ alkyl, an aryl group and a nitrogen-containing heterocyclyl group, or may form a ring containing a nitroxide radical(s) together with two adjacent ring atoms of the aromatic ring or the nitrogen-containing hetero ring; with the proviso that at least one nitroxide radical is present in the compound.

14. The method according to claim 12, wherein the porphyrin or the phthalocyanine with a nitroxide radical(s) is a compound of the following formula II:

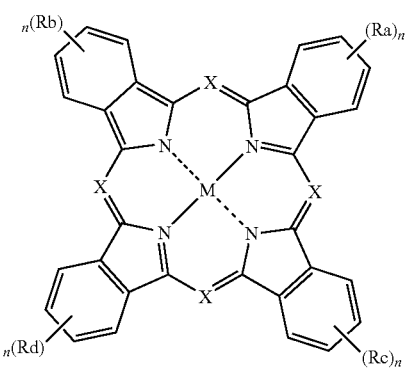

wherein

X is N or CR', where R' is a hydrogen atom, a $C_{1-18}$ alkyl group, an aryl group or a nitrogen-containing heterocyclyl group;

M is H$_2$ or an atom selected from elements of Groups 2-4 or Groups 8-15 of the Periodic Table;

when M is an atom selected from elements of Groups 2-4 or Groups 8-15 of the Periodic Table, 1 or 2 axial ligands L may be present, where each L is independently a halogen atom, a hydroxyl group, a tri($C_{1-18}$ alkyl)silyloxy group or a nitroxide radical;

each n is independently 0, 1, 2, 3 or 4; and

Ra, Rb, Rc and Rd are, independently of one another, a halogen atom, a hydroxyl group, a sulfo group, a carboxyl group, a $C_{1-18}$ alkyl group, a $C_{1-18}$ alkoxy group, —S(O)$_{0-2}$—$C_{1-18}$ alkyl, —(OCH$_2$CH$_2$)$_{1-8}$—O—$C_{1-6}$ alkyl, an aryl group or a nitrogen-containing heterocyclyl group, or when n is 2, two adjacent groups of each Ra, Rb, Re and Rd may form a ring containing a nitroxide radical(s) together with ring atoms to which they are bonded;

with the proviso that at least one nitroxide radical is present in the compound.

15. The method according to claim 14, wherein M is an atom selected from elements of Group 2 or Groups 12-15 of the Periodic Table, and 1 or 2 axial ligands L are present.

16. The method according to claim 14, wherein the ring containing a nitroxide radical(s) formed together with the ring atoms is 2,2,6,6-tetramethyl-1-piperidinyloxy (TEMPO) or 2,2,5,5-tetramethyl-1-pyrrolidinyloxy (PROXYL).

17. The method according to claim 12, wherein the porphyrin or the phthalocyanine with a nitroxide radical(s) is a complex of the following formula III:

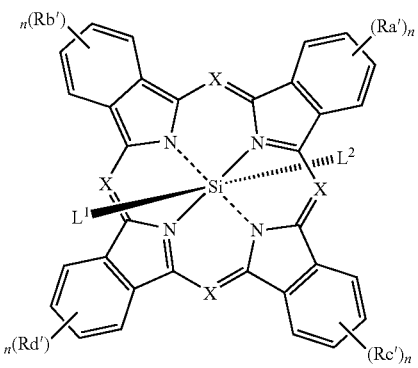

wherein

X is N or CR', where R' is a hydrogen atom, a $C_{1-18}$ alkyl group, an aryl group or a nitrogen-containing heterocyclyl group;

one of $L^1$ and $L^2$ is a nitroxide radical, and the other is a halogen atom, a hydroxyl group, a tri($C_{1-18}$ alkyl)silyloxy group or a nitroxide radical;

Ra', Rb', Rc' and Rd' are, independently of one another, a halogen atom, a hydroxyl group, a sulfo group, a carboxyl group, a $C_{1-18}$ alkyl group, a $C_{1-18}$ alkoxy group, —S(O)$_{0-2}$—$C_{1-18}$ alkyl, —(OCH$_2$CH$_2$)$_{1-8}$—O—$C_{1-6}$ alkyl, an aryl group or a nitrogen-containing heterocyclyl group; and each n is independently 0, 1, 2, 3 or 4.

18. The method according to claim 17, wherein X is N.

19. The method according to claim 17, wherein the nitroxide radical in $L^1$ or $L^2$ is of the following formula IV:

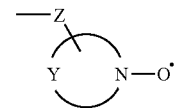

wherein

Y, together with N, forms a 5- to 6-membered, saturated or partially unsaturated, nitrogen-containing hetero ring, where the two atoms adjacent to the >N—O. group are tertiary carbon atoms, and the nitrogen-containing hetero ring optionally includes an additional N or O atom; and Z is a single bond or a spacer.

20. The method according to claim 19, wherein the nitroxide radical is a group comprising a 5- to 6-membered, saturated or partially unsaturated, nitrogen-containing hetero ring structure selected from 2,2,6,6-tetramethyl-1-piperidinyloxy (TEMPO), 2,2,5,5-tetramethyl-1-pyrrolidinyloxy (PROXYL), 4,4-dimethyl-3-oxazolidinyloxy (DOXYL) or nitronylnitroxide (NN).

Effect of the Invention

The basic procedure of the method for determination of vitamin C according to the present invention is a simple procedure in which a sample is simply contacted with a fluorogenic probe and the time-profile of luminescence intensity is measured (without the need to precisely adjust the concentration of the complex), and accurate determination can be made. Since the determination is made based on the time-profile of the luminescence intensity, the sample can be a solution or a suspension. Thus, complicated procedures such as device adjustment or sample pretreatment required in the HPLC method, or titration required for the indophenol method, are not necessary.

The method for detection of vitamin C in vivo according to the present invention is particularly suited for biofluorescent imaging because (1) the phthalocyanine with a nitroxide radical(s) incorporated into the liposomes reaches the intracellular space (see K. Ishii et al., Free Radical Biology & Medicine 38, 920-927 (2005); and K. Ishii et al., Seisan Kenkyu Vol. 60 (2) (2008), p. 160-163, for example), (2) the wavelength of the excitation light and luminescence of the fluorogenic probe (reduced form) is in a range of high permeability to biological tissue (>650 nm), and (3) reduction of the nitroxide radical(s) increases the luminescence intensity significantly. In other words, by following the time-profile of luminescence increase with a fluorescence microscope it is possible to know the distribution of vitamin C level in vivo, and therefore it is expected to be useful as a tool for elucidating the in vivo function of vitamin C. Furthermore, a liposome preparation is expected to be advantageous in terms of selectivity, since the luminescence intensity is not affected by reactive substances other than vitamin C (divalent iron ion, superoxide, etc.).

Recently, it has been reported that addition of a compound with a nitroxide radical of the following formula:

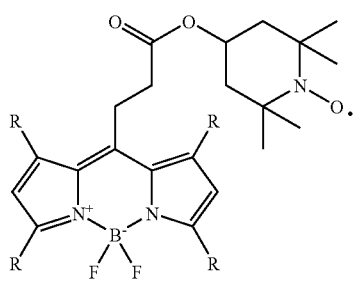

R = H or Me to cells as a water-soluble fluorogenic probe causes an oxidation-reduction reaction with intracellular reducing substances immediately after introducing it into the cells, resulting in reduction of the nitroxide radical in the fluorogenic probe and producing an observable increase in the luminescence intensity (see Yang Liu et al., Chem. Lett. 38, 588-589 (2009), for example). However, as clearly shown by Examples 5 and 6 below, a liposome preparation containing a fluorogenic probe according to the invention is virtually unaffected by intracellular reducing substances even after introducing it into cells, so that only the increase in luminescence intensity due to administration of high dosage vitamin C is observed. A liposome preparation comprising a fluorogenic probe according to the present invention is therefore expected to be useful for detection and determination of vitamin C in vivo.

DETAILED DESCRIPTION OF THE INVENTION

Figure 1:
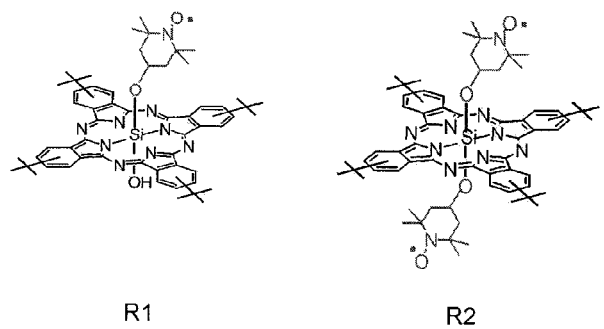
FIG. 1 is an illustration of the complexes R1 and R2 obtained in Preparation Example 1, as typical examples according to the present invention.

A porphyrin or a phthalocyanine with a nitroxide radical(s) according to the present invention is a porphyrin or a phthalocyanine comprising a nitroxide radical(s) in part of its chemical structure (for example, as an axial ligand, as a ring fused to the porphyrin or phthalocyanine ring, or as a substituent on the porphyrin or the phthalocyanine ring). According to the present invention, the terms "(a) porphyrin(s)" and "(a) phthalocyanine(s)" refer to "porphyrin or derivatives thereof" and "phthalocyanine or derivatives thereof", respectively. Thus, for the purpose of the present invention, the terms "porphyrin" and "phthalocyanine" include porphyrin and phthalocyanine as well as their analogs naphthalocyanine, 5,10,15,20-tetraazaporphyrin, subphthalocyanine and superphthalocyanine, and substituted derivatives thereof. Once the unpaired electrons of the nitroxide radical(s) is lost (they lose their radical nature), the compounds of the present invention exhibit increased luminescence intensity in the range of high permeability to biological tissue (>650 nm).

The porphyrin or phthalocyanine with a nitroxide radical(s) of the present invention is preferably a compound of the following formula I:

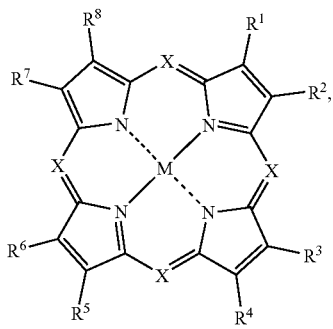

and more preferably a compound of the following formula II:

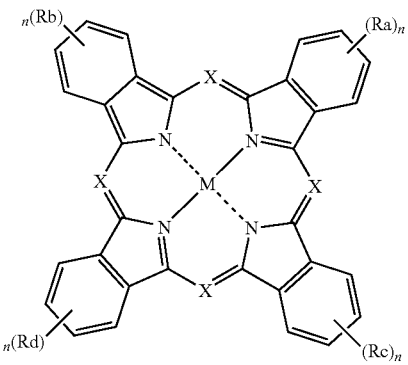

In formula I or II, X is N or CR', where R' is a hydrogen atom, a $C_{1-18}$ alkyl group, an aryl group or a nitrogen-containing heterocyclyl group. X is preferably N.

Also in formula I or II, M is $H_2$ (i.e. the compound is metal-free) or an atom selected from elements of Groups 2-4 or Groups 8-15 of the Periodic Table such as Mg, Al, Si, Sc, Ti, Cu, Zn, Ga, Ge, Y, Zr, Ru, Rh, Pd, Ag, Cd, In, Sn, La, Ce, Lu, Hf, Os, Ir, Pt, Au, Hg, Tl, Th or U. Preferably, M is an atom selected from elements of Group 2 or Groups 12-15 of the Periodic Table such as Mg, Al, Si, Zn, Ga, Ge, Cd, In or Sn.

More preferred are compounds wherein M is an atom selected from elements of Group 14 of the Periodic Table, with M most preferably being Si, and two axial ligands L are present, such as a complex of the following formula III:

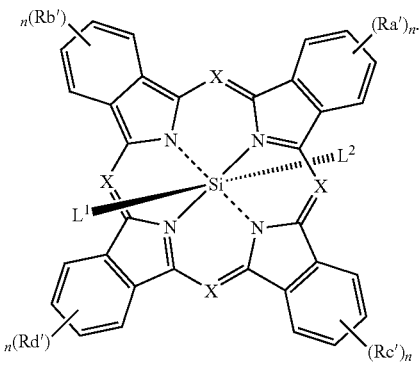

In formula III, X has the same definition as in formulas I and II, and it is preferably N. Specifically, it is preferably a (phthalocyaninato)silicon complex with a nitroxide radical(s) as an axial ligand(s).

In formula I or II, the nitroxide radical(s) may be present as the axial ligand(s) L if M is an atom selected from elements of Groups 2-4 or Groups 8-15 of the Periodic Table, or in formula I, it may be present as the substituent $R^1$, $R^2$, $R^3$, $R^4$, $R^5$, $R^6$, $R^7$ or $R^8$ on the porphyrin or phthalocyanine ring. One of the axial ligands $L^1$ and $L^2$ in the compound of formula III is a nitroxide radical. A nitroxide radical as such an axial ligand or a substituent may be a group comprising >N—O., but it is preferably of the following formula IV:

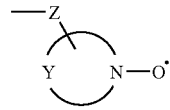

In formula IV, Y together with N forms a 5- to 6-membered, saturated or partially unsaturated, nitrogen-containing hetero ring, where the two atoms adjacent to the >N—O. group are tertiary carbon atoms, and the nitrogen-containing hetero ring optionally includes an additional N or O atom. The nitroxide radical is preferably a group comprising a 5- to 6-membered, saturated or partially unsaturated, nitrogen-containing hetero ring structure selected from 2,2,6,6-tetramethyl-1-piperidinyloxy (TEMPO), 2,2,5,5-tetramethyl-1-pyrrolidinyloxy (PROXYL), 4,4-dimethyl-3-oxazolidinyloxy (DOXYL) or nitronylnitroxide (NN).

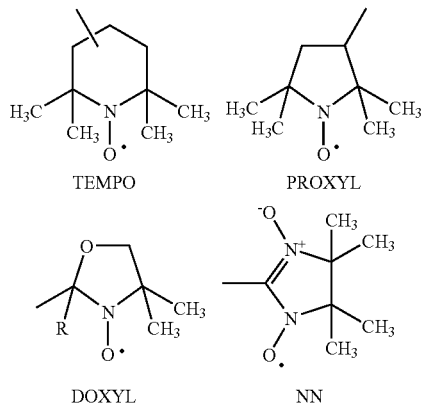

wherein, R represents $C_{1-18}$ alkyl or the like.

In formula IV, Z is a single bond or a spacer to the central atom M of the complex or the porphyrin or phthalocyanine ring, such as —O—, —$(CH_2)_{1-18}$—, —CO—, —COO—, —OCO—, —NH—, —NHCO— or —CONH—, or a combination thereof.

Alternatively, the nitroxide radical in formula I or II may be present as a ring fused to the porphyrin or phthalocyanine ring. Specifically, $R^1$ and $R^2$, $R^3$ and $R^4$, $R^5$ and $R^6$ and/or $R^7$ and $R^8$ in formula I "form an aromatic ring or a nitrogen-containing hetero ring together with the carbon atoms to which they are bonded, may form a ring containing a nitroxide radical(s) together with two adjacent ring atoms of the aromatic ring or the nitrogen-containing hetero ring", which means that a 5- to 6-membered, saturated or partially unsaturated, nitrogen-containing hetero ring comprising >N—O. group, where the two atoms adjacent to the >N—O. group are tertiary carbon atoms, is further formed together with two adjacent ring atoms of the aromatic ring or the nitrogen-containing hetero ring which $R^1$ and $R^2$, $R^3$ and $R^4$, $R^5$ and $R^6$ and/or $R^2$ and $R^8$ form together with the carbon atoms to which they are bonded. A preferred ring is a 5- to 6-membered, saturated or partially unsaturated, nitrogen-containing hetero ring such as TEMPO, PROXYL, DOXYL or NN as mentioned above. TEMPO or PROXYL is especially preferred.

Similarly, the phrase "when n is 2, the two adjacent groups of each Ra, Rb, Rc and Rd may form a ring containing a nitroxide radical(s) together with the ring atoms to which they are bonded" for formula II means that each of Ra, Rb, Rc and/or Rd, together with the two adjacent ring atoms, form a 5- to 6-membered, saturated or partially unsaturated, nitrogen-containing hetero ring comprising >N—O. group, where two atoms adjacent to the >N—O. group are tertiary carbon atoms, and the nitrogen-containing hetero ring may include an additional N or O atom. A preferred ring is a 5- to 6-membered, saturated or partially unsaturated, nitrogen-containing hetero rings such as TEMPO, PROXYL, DOXYL or NN as mentioned above. TEMPO or PROXYL is especially preferred. The following is an example of such compound of formula II:

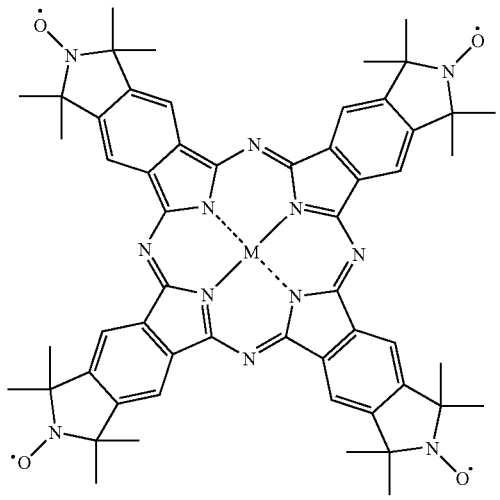

where M has the same definition as above. Such compound can be prepared by the method described in Anthony G. M. Barrett, et al., Tetrahedron 63 (24), 5244-5250 (2007), for example.

In formula I of the present invention, $R^1$, $R^2$, $R^3$, $R^4$, $R^5$, $R^6$, $R^7$ and $R^8$ are, independently of one another, a hydrogen atom, a $C_{1-18}$ alkyl group, a $C_{1-18}$ alkoxy group, an aryl group, a nitrogen-containing heterocyclyl group or a nitroxide radical, or $R^1$ and $R^2$ form an aromatic ring or a nitrogen-containing hetero ring together with the carbon atoms to which they are bonded, and the aromatic ring or the nitrogen-containing hetero ring is unsubstituted or substituted with one or more substituents selected from the group consisting of a halogen atom, a hydroxyl group, a sulfo group, a carboxyl group, a $C_{1-18}$ alkyl group, a $C_{1-18}$ alkoxy group, —$S(O)_{0-2}$—$C_{1-18}$ alkyl, —$(OCH_2CH_2)_{1-8}$—O—$C_{1-6}$ alkyl, an aryl group and a nitrogen-containing heterocyclyl group, or may form a ring containing a nitroxide radical(s) together with two adjacent ring atoms of the aromatic ring or the nitrogen-containing hetero ring, $R^3$ and $R^4$ form an aromatic ring or a nitrogen-containing hetero ring together with the carbon atoms to which they are bonded, and the aromatic ring or the nitrogen-containing hetero ring is unsubstituted or substituted with one or more substituents selected from the group consisting of a halogen atom, a hydroxyl group, a sulfo group, a carboxyl group, a $C_{1-18}$ alkyl group, a $C_{1-18}$ alkoxy group, —$S(O)_{0-2}$—$C_{1-18}$ alkyl, —$(OCH_2CH_2)_{1-8}$—O—$C_{1-6}$ alkyl, an aryl group and a nitrogen-containing heterocyclyl group, or may form a ring containing a nitroxide radical(s) together with two adjacent ring atoms of the aromatic ring or the nitrogen-containing hetero ring, $R^5$ and $R^6$ form an aromatic ring or a nitrogen-containing hetero ring together with the carbon atoms to which they are bonded, and the aromatic ring or the nitrogen-containing hetero ring is unsubstituted or substituted with one or more substituents selected from the group consisting of a halogen atom, a hydroxyl group, a sulfo group, a carboxyl group, a $C_{1-18}$ alkyl group, a $C_{1-18}$ alkoxy group, —$S(O)_{0-2}$—$C_{1-18}$ alkyl, —$(OCH_2CH_2)_{1-8}$—O—$C_{1-6}$ alkyl, an aryl group and a nitrogen-containing heterocyclyl group, or may form a ring containing a nitroxide radical(s) together with two adjacent ring atoms of the aromatic ring or the nitrogen-containing hetero ring, or $R^7$ and $R^8$ form an aromatic ring or a nitrogen-containing hetero ring together with the carbon atoms to which they are bonded, and the aromatic ring or the nitrogen-containing hetero ring is unsubstituted or substituted with one or more substituents selected from the group consisting of a halogen atom, a hydroxyl group, a sulfo group, a carboxyl group, a $C_{1-18}$ alkyl group, a $C_{1-18}$ alkoxy group, —$S(O)_{0-2}$—$C_{1-18}$ alkyl, —$(OCH_2CH_2)_{1-8}$—O—$C_{1-6}$ alkyl, an aryl group and a nitrogen-containing heterocyclyl group, or may form a ring containing a nitroxide radical(s) together with two adjacent ring atoms of the aromatic ring or the nitrogen-containing hetero ring.

The phrase "$R^1$ and $R^2$ form an aromatic ring or a nitrogen-containing hetero ring together with the carbon atoms to which they are bonded" means that $R^1$ and $R^2$, together with the two carbon atoms of the pyrrole ring portion to which they are bonded, form an aromatic ring such as a benzene or naphthalene ring, or a 5- to 6-membered, saturated, partially unsaturated or unsaturated ring containing at least one nitrogen atom, preferably one or two nitrogen atoms, such as a pyridine or pyrazine ring. The same definitions found in "$R^3$ and $R^4$", "$R^5$ and $R^6$", "$R^7$ and $R^8$" are the same as stated above.

The compounds of formula II of the present invention correspond to compounds of formula I wherein each of $R^1$ and $R^2$, $R^3$ and $R^4$, $R^5$ and $R^6$ and $R^7$ and $R^8$ forms a benzene ring together with carbon atoms to which they are bonded. In formula II, therefore, Ra, Rb, Rc and Rd are, independently of one another, a halogen atom, a hydroxyl group, a sulfo group, a carboxyl group, a $C_{1-18}$ alkyl group, a $C_{1-18}$ alkoxy group, —$S(O)_{0-2}$—$C_{1-18}$ alkyl, —$(OCH_2CH_2)_{1-8}$—O—$C_{1-6}$ alkyl, an aryl group or a nitrogen-containing heterocyclyl group, or when n is 2, two adjacent groups of each Ra, Rb, Rc and Rd may form a ring containing a nitroxide radical(s) together with ring atoms to which they are bonded, and each n is independently 0, 1, 2, 3 or 4.

The complexes of formula III of the present invention correspond to compounds of formula II wherein M is Si (silicon) having axial ligands $L^1$ and $L^2$, at least one of which is a nitroxide radical. In formula III, therefore, Ra', Rb', Rc' and Rd' are, independently of one another, a halogen atom, a hydroxyl group, a sulfo group, a carboxyl group, a $C_{1-18}$ alkyl group, a $C_{1-18}$ alkoxy group, $-S(O)_{0-2}-C_{1-18}$ alkyl, $-(OCH_2CH_2)_{1-8}-O-C_{1-6}$ alkyl, an aryl group or a nitrogen-containing heterocyclyl group, and each n is independently 0, 1, 2, 3 or 4.

Throughout the present specification and claims, the term "a halogen atom" refers to fluorine, chlorine, bromine or iodine, unless otherwise specified. Preferably, it is chlorine.

The term "a $C_{1-18}$ alkyl group", unless otherwise specified, means a straight-chain or branched-chain, saturated hydrocarbon group having 1-18 carbon atoms, either alone or in combination with other terms. As examples there may be mentioned methyl, ethyl, n-propyl, iso-propyl, n-butyl, iso-butyl, sec-butyl, tert-butyl, n-pentyl, n-hexyl, n-heptyl, n-octyl, decyl, dodecyl, octadecyl and the like. $C_{1-8}$ alkyl groups are preferred.

Also, unless other specified, the term "a $C_{1-18}$ alkoxy group" refers to "a $C_{1-18}$ alkyl group" as described above bonded through an oxygen atom, or in other words a $C_{1-18}$ alkyl-O-group. As examples there may be mentioned methoxy, ethoxy, n-propoxy, iso-propoxy, n-butoxy, iso-butoxy, sec-butoxy, tert-butoxy, n-pentyloxy, n-hexyloxy, n-heptyloxy, n-octyloxy, decyloxy, dodecyloxy, octadecyloxy and the like. $C_{1-8}$ alkoxy groups are preferred.

Similarly, unless other specified, the term "a tri($C_{1-18}$ alkyl)silyloxy group" refers to a group wherein the three "$C_{1-18}$ alkyl" portions, which may be the same or different, is selected from "a $C_{1-18}$ alkyl group" described above. As examples of such tri($C_{1-18}$ alkyl)silyloxy groups there may be mentioned trimethylsilyloxy, triethylsilyloxy, tri-iso-propyl-silyloxy, tri-n-hexylsilyloxy, decyl-dimethylsilyloxy, dimethyl-octadecylsilyloxy and the like.

Unless other specified, the term "$-S(O)_{0-2}-C_{1-18}$ alkyl" includes $-S-C_{1-18}$ alkyl, $-S(O)-C_{1-18}$ alkyl and $-S(O)_2-C_{1-18}$ alkyl. Preferred groups are $-S-C_{1-8}$ alkyl, $-S(O)-C_{1-8}$ alkyl and $-S(O)_2-C_{1-8}$ alkyl, such as methylthio or ethylthio. The term "$-(OCH_2CH_2)_{1-8}O-C_{1-6}$ alkyl" refers to an ethyleneglycol group with 1-8 oxyethylene ($OCH_2CH_2$) units. It is preferably $-(OCH_2CH_2)_{2-4}O-C_{1-6}$ alkyl, such as 3,6,9-trioxadecyloxy, for example.

Also, unless other specified, the term "an aryl group" refers to a monovalent group of aromatic mono- or poly-carbocyclic compound having 6-14 carbon atoms, either alone or in combination with other terms. As examples there may be mentioned phenyl, naphthyl, anthryl, phenanthryl, and the like. "An aryl group" may be unsubstituted or substituted with one or more substituents selected from the group consisting of a halogen atom, a hydroxyl group, a sulfo group, a carboxyl group, a $C_{1-18}$ alkyl group, a $C_{1-18}$ alkoxy group and a phenyl group. Preferred aryl group is phenyl or naphthyl.

Similarly, unless other specified, the term "a nitrogen-containing heterocyclyl group" refers to a monovalent group of a 5- to 6-membered, saturated, partially unsaturated or unsaturated ring containing at least one nitrogen atom, preferably one or two nitrogen atoms, either alone or in combination with other terms. "A nitrogen-containing heterocyclyl group" may be unsubstituted or substituted with one or more substituents selected from the group consisting of a halogen atom, a hydroxyl group, a sulfo group, a carboxyl group, a $C_{1-18}$ alkyl group, a $C_{1-18}$ alkoxy group and a phenyl group, or may form an onium from by an addition of proton or a $C_{1-8}$ alkyl group to the at least one nitrogen atom. Preferred nitrogen-containing heterocyclyl group is pyridyl, pyrazinyl or an onium compound thereof (N-methyl-pyridiniumyl, for example).

Table 1 below lists representative examples of the porphyrins or the phthalocyanines with a nitroxide radical(s) to be used as fluorogenic probes according to the invention.

TABLE 1

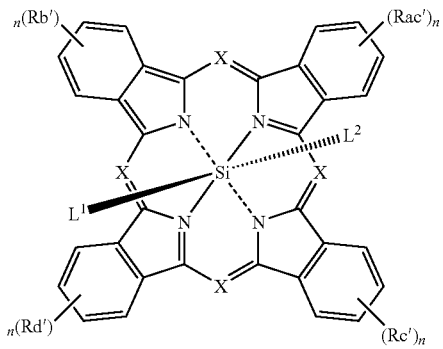

| | X | $L^1$ | $L^2$ | Ra'—Rd' | n |
|---|---|---|---|---|---|
| R0 | N | —OH | —OH | —C(CH$_3$)$_3$ | 1 |
| R1 | N | (structure) | —OH | —C(CH$_3$)$_3$ | 1 |

TABLE 1-continued

| X | L¹ | L² | Ra'—Rd' | n |
|---|---|---|---|---|
| R2 | N | methoxy-tetramethylpiperidine-N-oxyl ether | methoxy-tetramethylpiperidine-N-oxyl ether | —C(CH₃)₃ | 1 |
| R3 | N | methoxy-tetramethylpyrrolidine-N-oxyl ether | —OH | —C(CH₃)₃ | 1 |
| R4 | N | methoxy-tetramethylpyrrolidine-N-oxyl ether | methoxy-tetramethylpyrrolidine-N-oxyl ether | —C(CH₃)₃ | 1 |
| R5 | N | methyl tetramethylpiperidine-N-oxyl-4-carboxylate | —OH | —C(CH₃)₃ | 1 |
| R6 | N | methyl tetramethylpyrrolidine-N-oxyl-3-carboxylate | —OH | —C(CH₃)₃ | 1 |

The (phthalocyaninato)silicon complexes R1-R6 shown in Table 1 as examples of the present invention can be produced by the methods described in references mentioned above (see K. Ishii et al., J. Porphyrins Phthalocyanines 3, 439-443 (1999); K. Ishii et al., J. Am. Chem. Soc. 123 (4), 702-708 (2001); K. Ishii et al., J. Phys. Chem. A 105 (28), 6794-6799 (2001); and K. Ishii et al., J. Phys. Chem. A 108 (16), 3276-3280 (2004), for example) or the procedures described in the examples given below. A person skilled in the art can produce any porphyrin or phthalocyanine with a nitroxide radical(s) according to the present invention, and particularly a compound of formula I, II or III, based on these methods and common technical knowledge.

A liposome preparation of the present invention is a preparation comprising such a porphyrin or phthalocyanine with a nitroxide radical(s) encapsulated into closed vesicles (liposomes) composed of lipid bilayers. For example, a liposome preparation of the present invention may comprise a porphyrin or phthalocyanine with a nitroxide radical(s) according to the present invention encapsulated into unilamellar or multilamellar liposomes formed from a phospholipid, such as an egg yolk- or soybean-derived natural phospholipid, or a synthetic phospholipid such as dimyristoylphosphatidylcholine, distearoylphosphatidylcholine or dipalmitoylphosphatidylcholine. It may be in fine particulate form, or in solution or suspension form containing fine particles. The liposome preparation can be produced by a method known to those skilled in the art or a procedure described in the examples given below. An auxiliary agent other than the active ingredients, such as a saccharide (lactose, mannitol or the like), neutral lipid (cholesterol, a triglyceride or the like) or a charged lipid (phosphatidic acid, stearylamine or the like) may be added, or any membrane modification of the liposomes according to known method may also be conducted in order to impart desired properties.

The method for detection and determination of vitamin C by luminescence according to the present invention comprises (1) a step of contacting a fluorogenic probe or liposome preparation according to the present invention with a sample under irradiation with excitation light at a wavelength of 650 nm or greater; and (2) a step of monitoring the luminescence. The sample may be prepared by first preparing a solution or suspension of a (putatively) vitamin C-containing specimen in water, a buffering solution or an organic solvent that can dissolve vitamin C, such as methanol, or a mixture of the foregoing, to a suitable concentration, or if the specimen is a liquid, by using it directly or after appropriate pretreatment.

Figure 2:
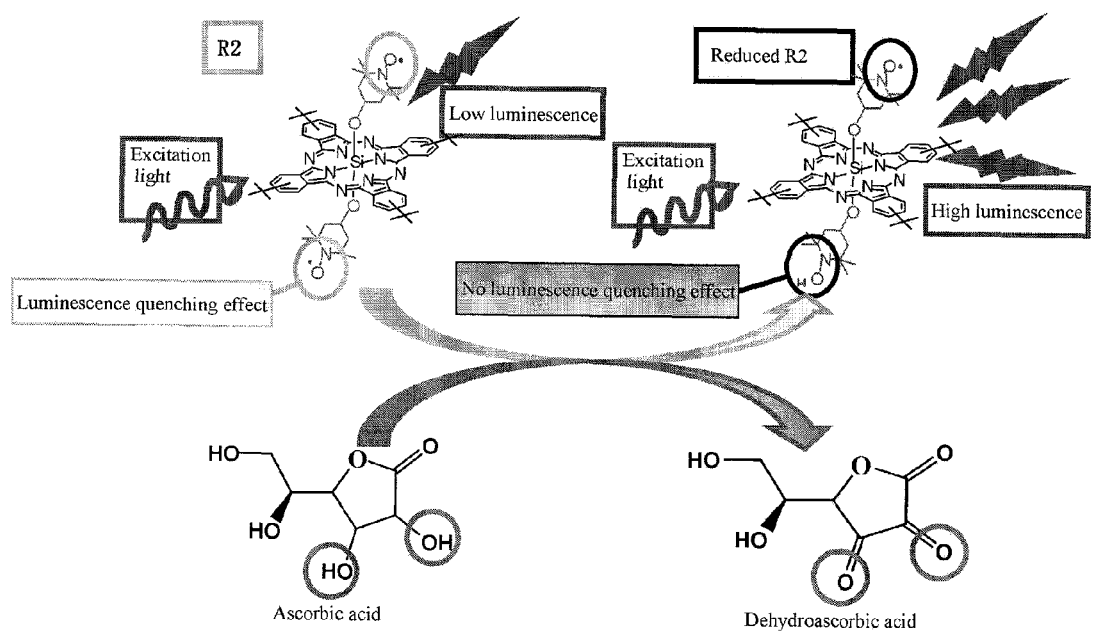
FIG. 2 is a schematic of the reaction system in the method of detection and determination of vitamin C by luminescence according to the present invention.

The method for detection and determination of vitamin C by luminescence according to the present invention includes monitoring of the increase in luminescence intensity that occurs when a fluorogenic probe of the present invention, i.e. a porphyrin or phthalocyanine with a nitroxide radical(s), is contacted with vitamin C to reduce the nitroxide radical and convert it to a reduced form not having the unpaired electron (that is, the luminescence quenching effect of the nitroxide radical is lost) (see the schematic of reaction system shown in FIG. 2). It is a feature of the present invention that the increase in luminescence intensity occurs in a range of high permeability to biological tissue (>650 nm) (see FIG. 7, for example). Thus, the excitation light may be set to a wavelength of 650 nm or greater, and preferably near the maximum excitation wavelength of the reduced form, and the emitted light may also be monitored near the maximum fluorescence wavelength of the reduced form.

The method for determination of vitamin C according to the invention further comprises (2) a step of monitoring luminescence and measuring the time-profile of luminescence intensity; and (3) determining the concentration of vitamin C in the sample. We have found that a correlation exists between vitamin C concentration and the reaction rate constant calculated from the time-profile of the luminescence intensity (see Examples 1-4 below). Vitamin C is a two-electron reducing agent, but since the first electron reduction is the rate-determining step, the reaction between vitamin C and the fluorogenic probe consisting of a porphyrin or phthalocyanine with one nitroxide radical in methanol, for example, can be understood as a second order reaction (pseudo-first-order reaction), while the reaction between vitamin C and a fluorogenic probe consisting of a porphyrin or phthalocyanine with two nitroxide radicals can be understood as the consecutive reaction. We have confirmed that when a liposome preparation comprising a fluorogenic probe consisting of a porphyrin or phthalocyanine with 1 or 2 nitroxide radicals is used, both can be understood as second order reactions (pseudo-first-order reactions). A person skilled in the art, therefore, can analyze the time-profile of luminescence intensity with an appropriate reaction rate equation to calculate the rate constant. Thus, the method for determining vitamin C according to the present invention is a very simple method that allows the rate constant to be calculated based on analysis of the time-profile of luminescence intensity, so that the concentration can be determined using a calibration curve.

The methods for detection and determination of vitamin C can be applied as methods for detecting vitamin C in vivo. The method for detection of vitamin C in vivo, according to the present invention, comprises (1) a step of administering a liposome preparation of the present invention to a subject; and (2) a step of irradiating the subject with excitation light of wavelength of 650 nm or greater and monitoring the luminescence. We have already reported that a (phthalocyaninato) silicon complex having a nitroxide radical as an axial ligand, incorporated into liposomes, reaches the intracellular space and is minimally affected by oxidation-reduction in vivo (see K. Ishii et al., Free Radical Biology & Medicine 38, 920-927 (2005); and K. Ishii et al., Seisan Kenkyu Vol. 602 (2008), p. 160-163, for example). Evidence provided in the present specification confirms that the liposome preparation reacts with vitamin C and exhibits an increase in luminescence intensity in a range of high permeability to biological tissue. A fluorogenic probe or liposome preparation of the present invention, therefore, is fully expected to be applicable for biofluorescent imaging of vitamin C.

EXAMPLES

Preparation Example 1

Preparation of Complexes R1 and R2 (see FIG. 1 or Table 1)

Dihydroxy(tetra-tert-butyl phthalocyaninato)silicon (SiPc $(OH)_2$) (R0 listed in Table 1) can be obtained by the method described in Macromolecules, 11 (1), 186-191 (1978). SiPc $(OH)_2$ (50 mg) and 2,2,6,6-tetramethyl-4-piperidinol-1-oxyl (430 mg, Cat.-No. 176141, purchased from Sigma-Aldrich Co.; hereinafter referred to as "4-hydroxy-TEMPO") were heated to reflux for 48 hours in toluene, in the presence of calcium chloride (2 g). After cooling the obtained mixture, it was purified by basic alumina and gel filtration chromatography (Bio-Beads SX-1, purchased from Bio-Rad), to obtain complexes R1 and R2 at yields of 40% and 15%, respectively.

R1 elemental analysis ($C_{57}H_{66}N_9O_3Si$):
Calculated: C, 71.82; H, 6.98; N, 13.22%.
Found: C, 70.84; H, 7.08; N, 12.44%.
R2 elemental analysis ($C_{66}H_{82}N_{10}O_4Si$):
Calculated: C, 71.56; H, 7.48; N, 12.65%.
Found: C, 70.98; H, 7.05; N, 12.51%.

Preparation Example 2

Preparation of Complex R3 (see Table 1)

Complex R3 was obtained at a yield of 37% in the same manner as Preparation Example 1, except that 3-hydroxy-2,2,5,5-tetramethyl-1-pyrrolidinyloxy [hereinafter referred to as "3-hydroxy-PROXYL"; prepared from 3-carbamoyl-2,2,5,5-tetramethyl-1-pyrrolidinyloxy (Cat.-No. C5151, purchased from Sigma-Aldrich Co.) by the method described in E. G. Rozantsev et. al., Tetrahedron 21, 491 (1965)] was used instead of 4-hydroxy-TEMPO, and the reflux time was 24 hours.

UV-vis ($\lambda/nm(\epsilon/10^4)$) 685.0 (28.0), 651.0 (3.76), 612.0 (4.41), 360.0 (8.90);
FAB mass m/e 938 ($M^+$);
Elemental analysis ($C_{56}H_{64}N_9O_3Si$):
Calculated: C, 71.61; H, 6.87; N, 13.42%.
Found: C, 70.893; H, 6.633; N, 12.766%.

Preparation Example 3

Preparation of Complex R4 (see Table 1)

Complex R4 was obtained at a yield of 19% in the same manner as Preparation Example 1, except that 3-hydroxy-PROXYL was used instead of 4-hydroxy-TEMPO and the reflux time was 42 hours.

UV-vis ($\lambda$/nm($\epsilon$/10$^4$)) 682.5 (26.0), 651.5 (3.45), 613.5 (4.19), 359.5 (8.69);
ESI-TOF m/e 1079 (M$^+$);
Elemental analysis ($C_{64}H_{78}N_{10}O_4Si$):
Calculated: C, 71.21; H, 7.28; N, 12.98%.
Found: C, 70.459; H, 7.402; N, 12.783%.

Preparation Example 4

Preparation of Complex R5 (see Table 1)

SiPc(OH)$_2$ and 4-carboxy-2,2,6,6-tetramethylpiperidine-1-oxyl (Cat.-No. 382,000, purchased from Sigma-Aldrich Co.; hereinafter referred to as "4-carboxy-TEMPO") were heated to reflux for 24 hours in pyridine. After cooling the obtained mixture, it was purified by neutral alumina and gel filtration chromatography (Bio-Beads SX-1 or SX-8, purchased from Bio-Rad), to obtain complex R5 at a yield of 9%.
UV-vis ($\lambda$/nm($\epsilon$/10$^4$)) 685.5 (24.2), 656.0 (3.33), 616.5 (3.72), 362.5 (7.64);
FAB mass m/e 980 (M$^+$);
Elemental analysis ($C_{58}H_{66}N_9O_4Si$):
Calculated: C, 70.99; H, 6.78; N, 12.85%.
Found: C, 71.997; H, 7.133; N, 11.955%.

Preparation Example 5

Preparation of Complex R6 (see Table 1)

Complex R6 was obtained at a yield of 15% in the same manner as Preparation Example 4, except that 3-carboxy-2,2,5,5-tetramethyl-1-pyrrolidinyloxy (Cat.-No. 253324, purchased from Sigma-Aldrich Co.; hereinafter referred to as "3-carboxy-PROXYL") was used instead of 4-hydroxy-TEMPO.
UV-vis ($\lambda$/nm($\epsilon$/10$^4$)) 685.0 (23.6), 653.0 (3.61), 616.5 (3.77), 362.0 (7.75);
FAB mass m/e 966 (M$^+$);
Elemental analysis ($C_{57}H_{64}N_9O_4Si$):
Calculated: C, 70.78; H, 6.67; N, 13.03%.
Found: C, 70.622; H, 6.503; N, 12.251%.

Example 1

Vitamin C Determining Experiment Using Complex R1 (in Methanol Solution)

Experiment Procedure (1) A $5.6 \times 10^{-6}$ M solution of complex R1 obtained in Preparation Example 1 in methanol was prepared.
(2) 64 mM, 16 mM, 8 mM and 4 mM solutions of Vitamin C in methanol were prepared.
(3) In a glass cell there were placed 1.8 ml of the solution obtained in the above (1) and a microstir bar, and the mixture was stirred with a stirrer (1000 r.p.m).
(4) The stirred mixture was irradiated with a diode laser (manufactured by Yamaki; LDX-2615-650-TO3; wavelength: 650 nm) as excitation light, the luminescence was monitored at 680 nm using a spectrometer (manufactured by JASCO Co.; CT-25TP) and a photomultiplier (manufactured by Hamamatsu Photonics K.K.; R928), while adding 0.2 ml of the vitamin C methanol solution obtained in the above (2), and the time-profile of luminescence intensity was measured. During this time, the angle and positional relationship were adjusted so that the optical fibers did not capture diffuse reflection from the microstir bar.
(5) The data were used for analysis at least 300 seconds after addition of the vitamin C, in consideration of contribution of non-uniform diffusion.

[Experimental Results]

Figure 3:
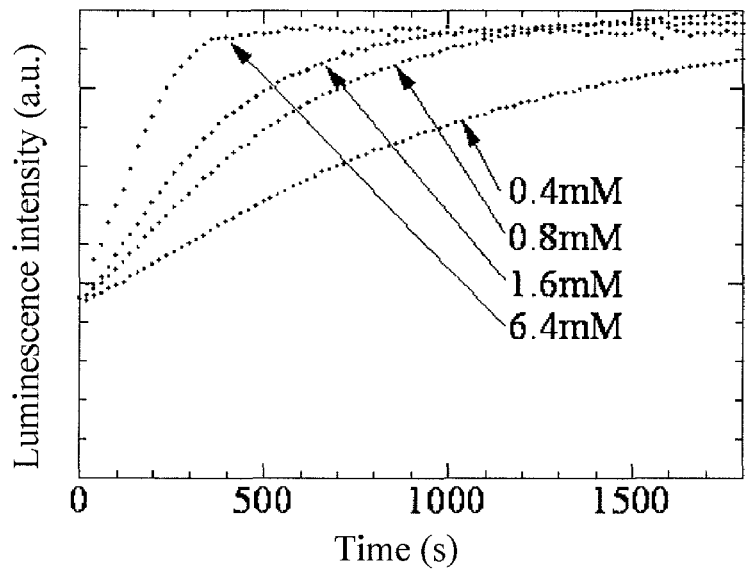
FIG. 3 is a graph showing the time-profile of luminescence intensity obtained in the vitamin C determination experiment of Example 1.
Figure 4:
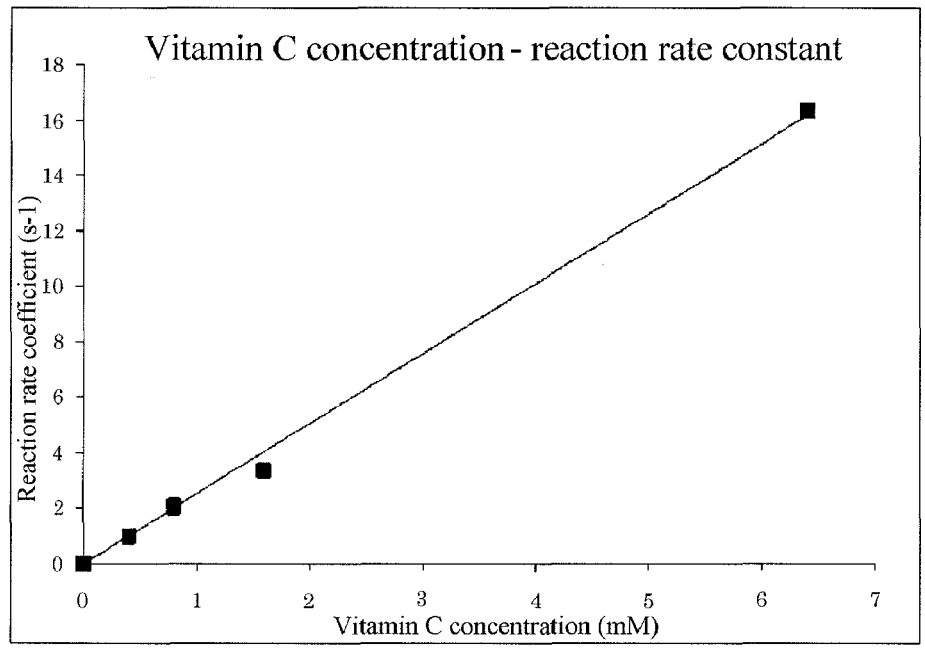
FIG. 4 is a graph showing the correlation between reaction rate constant and vitamin C concentration obtained in the vitamin C determination experiment of Example 1.

The luminescence intensity time profiles are shown in FIG. 3. The data from at least 300 seconds after vitamin C addition were used for analysis of the pseudo-first-order reaction, to obtain a reaction rate constant. A positive correlation was found between the reaction rate constant and vitamin C concentration (FIG. 4). This indicated that vitamin C can be precisely quantified by this method.

Example 2

Vitamin C Determining Experiment Using Complex R1 (in Liposome Aqueous Solution)

Experiment Procedure (1) The quantity of 0.15 mg ($1.58 \times 10^{-7}$ mol) of complex R1 obtained in Preparation Example 1 was determined using the absorption spectrum.
(2) 20.9 mg ($2.86 \times 10^{-5}$ mol) of dipalmitoylphosphatidylcholine (DPPC) was dissolved in 3.6 ml of chloroform.
(3) R1 was placed in a round-bottom flask and 180 µl of THF was added. A chloroform solution containing the liposomes obtained in the above (2) was then added, and the solvent was removed with an evaporator.
(4) After adding 2.0 ml of PBS (phosphate buffered saline, D-PBS(−)) and 0.5 g of glass beads to the dried solid, the mixture was placed in a vortex mixer and subjected to ultrasonic treatment at 50° C. for 1 hour.
(5) After cooling, it was subjected to centrifugal separation (3500 r.p.m, 10 minutes, 4000 r.p.m, 10 minutes, at room temperature) to obtain a supernatant solution as the target product.
(6) 64 mM, 32 mM, 16 mM, 8 mM 4 mM and 2 mM solutions of Vitamin C in PBS (phosphate buffered saline, D-PBS(−)) were prepared.
(7) The solution of the above (5) was diluted with PBS (phosphate buffered saline, D-PBS(−)) in such a way that the absorbance at a peak wavelength is about Abs=0.5, 1.35 ml of the diluted solution and a microstir bar were placed in a glass cell, and the mixture was stirred with a stirrer (1000 r.p.m).
(8) The stirred mixture was irradiated with a diode laser (manufactured by Yamaki; LDX-2615-650-TO3; wavelength: 650 nm) as excitation light, the luminescence was monitored at 690 nm using a spectrometer (manufactured by JASCO Co.; CT-25TP) and a photomultiplier (manufactured by Hamamatsu Photonics K.K.; R928), while adding 0.15 ml of the vitamin C PBS solution obtained in the above (6), and the time-profile of luminescence intensity was measured. During this time, the angle and positional relationship were adjusted so that the optical fibers did not capture diffuse reflection from the microstir bar.

[Experimental Results]

Figure 5:
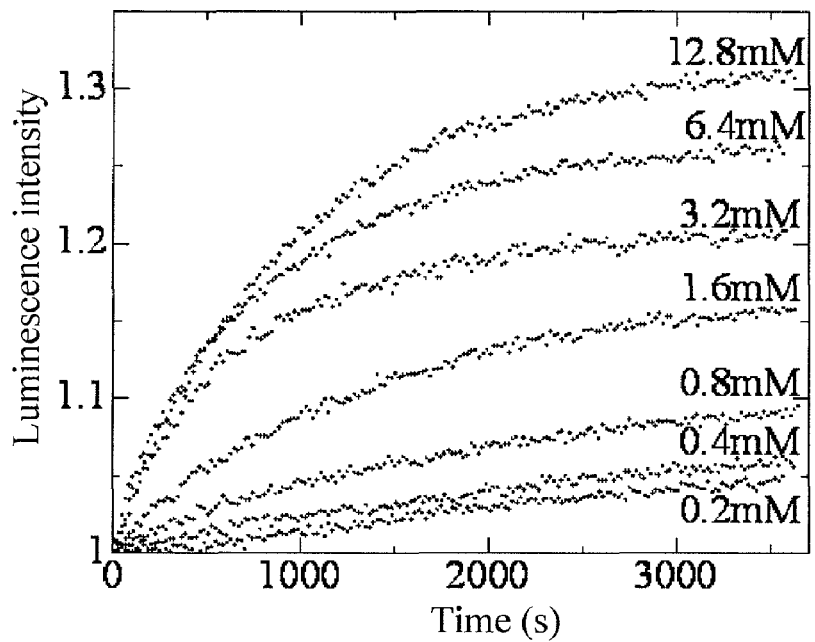
FIG. 5 is a graph showing the time-profile of luminescence intensity obtained in the vitamin C determination experiment of Example 2.

The luminescence intensity time profiles are shown in FIG. 5. The exponential increase in luminescence intensity was successfully observed, as in the methanol solution.

Example 3

Vitamin C Determining Experiment Using Complex R2 (in Methanol Solution)

Experiment Procedure (1) A $5 \times 10^{-6}$ M solution of complex R2 obtained in Preparation Example 1 in methanol was prepared.
(2) A 64 mM solution of vitamin C in methanol was prepared.
(3) In a glass cell there were placed 1.35 ml of the solution obtained in the above (1) and a microstir bar, and the mixture was stirred with a stirrer (1000 r.p.m).
(4) The stirred mixture was irradiated with a diode laser (manufactured by Yamaki; LDX-2615-650-TO3; wavelength: 650 nm) as excitation light, the luminescence was monitored at 686 nm using a spectrometer (manufactured by JASCO Co.; CT-25TP) and a photomultiplier (manufactured by Hamamatsu Photonics K.K.; R928) while adding 0.15 ml of the vitamin C methanol solution obtained in the above (2), and the time-profile of luminescence intensity was measured. During this time, the angle and positional relationship were adjusted so that the optical fibers did not capture diffuse reflection from the microstir bar.

[Experimental Results]

An approximately 6300% increase in luminescence intensity was observed.

Example 4

Vitamin C Determining Experiment Using Complex R2 (in Liposome Aqueous Solution)

Experiment Procedure (1) The quantity of 0.175 mg ($1.58 \times 10^{-7}$ mol) of complex R2 obtained in Preparation Example 1 was determined using the absorption spectrum.
(2) 20.9 mg ($2.86 \times 10^{-5}$ mol) of DPPC was dissolved in 3.6 ml of chloroform.
(3) R2 was placed in a round-bottom flask and 180 µl of THF was added. A chloroform solution containing the liposomes obtained in the above (2) was then added, and the solvent was removed with an evaporator.
(4) After adding 2 ml of PBS (phosphate buffered saline, D-PBS(−)) and 0.5 g of glass beads to the dried solid, the mixture was placed in a vortex mixer and subjected to ultrasonic treatment at 50° C. for 1 hour.
(5) After cooling, it was subjected to centrifugal separation (3500 r.p.m, 10 minutes, at room temperature) to obtain a supernatant solution as the target product.
(6) 128 mM, 64 mM, 16 mM, 8 mM, 4 mM and 2 mM solutions of Vitamin C in PBS (phosphate buffered saline, D-PBS(−)) were prepared.
(7) The solution of the above (5) was diluted with PBS (phosphate buffered saline, D-PBS(−)) in such a way that the absorbance at a peak wavelength is about Abs=1.4, 1.35 ml of the diluted solution and a microstir bar were placed in a glass cell, and the mixture was stirred with a stirrer (1000 r.p.m).
(8) The stirred mixture was irradiated with a diode laser (manufactured by Yamaki; LDX-2615-650-TO3; wavelength: 650 nm) as excitation light, the luminescence was monitored at 686 nm (700 nm for 12.8 mM) using a spectrometer (manufactured by JASCO Co.; CT-25TP) and a photomultiplier (manufactured by Hamamatsu Photonics K.K.; R928), while adding 0.15 ml of the vitamin C PBS solution obtained in the above (6), and the time-profile of luminescence intensity was measured. During this time, the angle and positional relationship were adjusted so that the optical fibers did not capture diffuse reflection from the microstir bar.

[Experimental Results]

Figure 6:
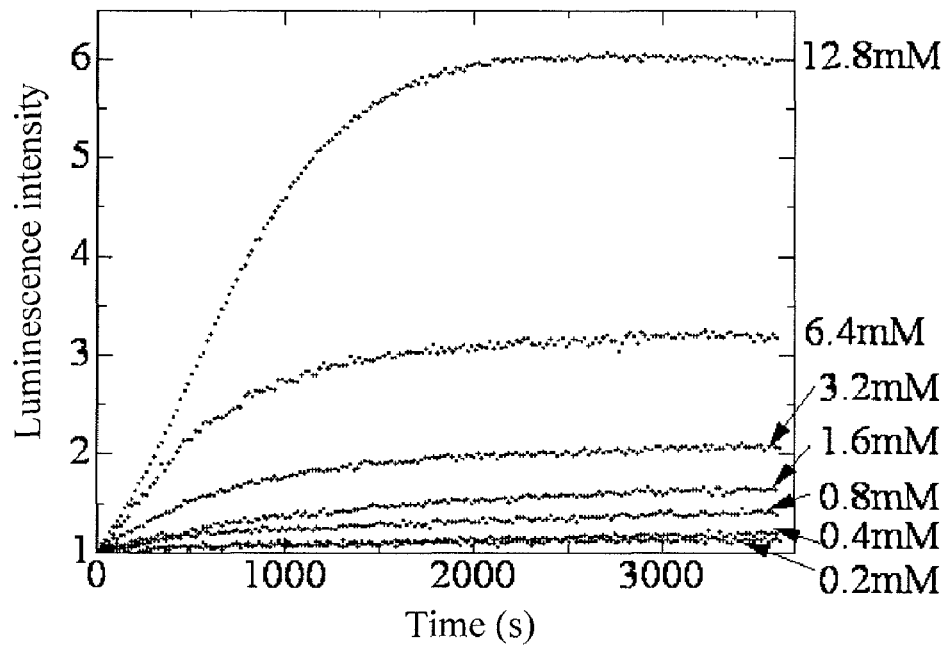
FIG. 6 is a graph showing the time-profile of luminescence intensity obtained in the vitamin C determination experiment of Example 4.
Figure 7:
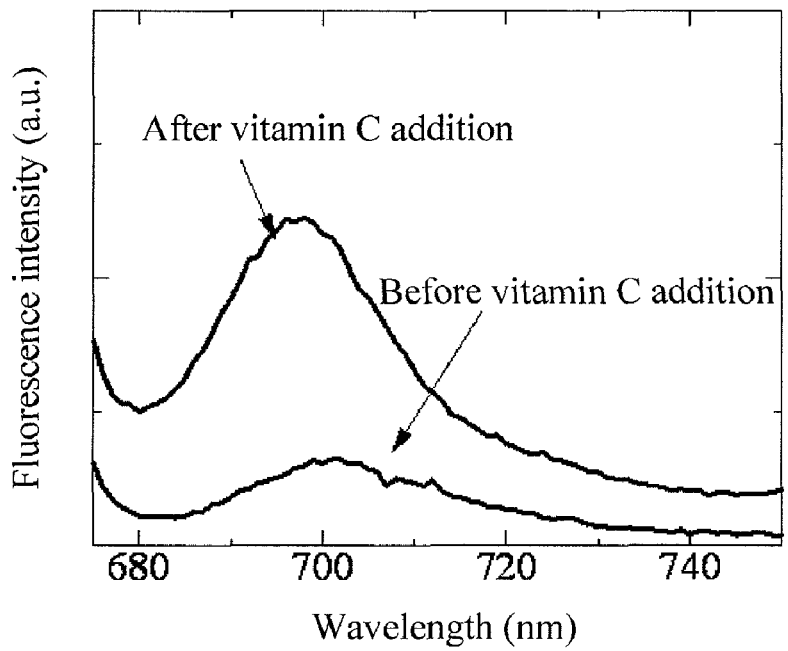
FIG. 7 shows luminescence emission spectra of the R2 liposome solution in Example 4, before and after vitamin C addition.
Figure 8:
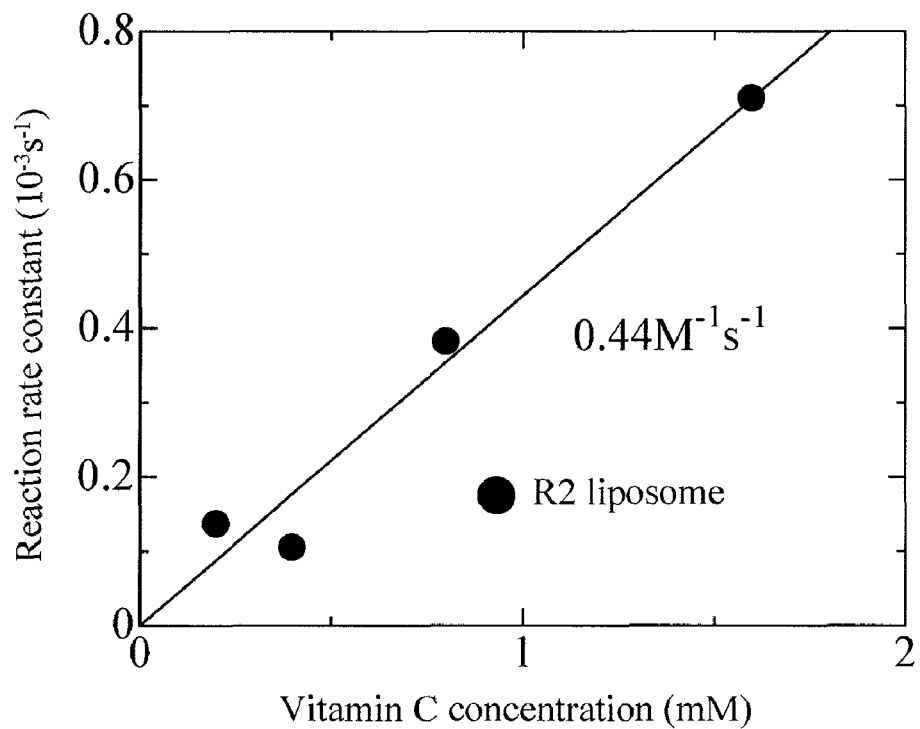
FIG. 8 is a graph showing the correlation between reaction rate constant and vitamin C concentration obtained in the vitamin C determination experiment of Example 4.

The luminescence intensity time profiles are shown in FIG. 6. A correlation was found between vitamin C concentration and luminescence intensity. Also, a 500% increase in luminescence intensity, which was a change in luminescence intensity considered sufficient for bioimaging, was observed (FIG. 7). In addition, the time-profile of luminescence intensity could be fit to a pseudo-first-order reaction, and a correlation between vitamin C concentration and reaction rate constant was seen in the low concentration range (FIG. 8). It is therefore expected to be applied to fluorescence bioimaging of vitamin C in cells used for research.

Example 5

Vitamin C Bioimaging Experiment in Cells

Experiment Procedure (1) A solution of complex R2 liposomes prepared by steps (1)-(5) in the above Example 4 (hereinafter referred to as "R2 liposomes") was diluted 10-fold with DMF, the amount of the photosensitizer (complex R2) encapsulated into the liposomes was calculated from the absorbance of the absorption spectrum to determine the concentration, and the concentration was adjusted.
(2) HeLa cells ($2 \times 10^4$ cells/cm$^2$, purchased from Health Sciences Research Resources Bank) of 5 ml of medium were inoculated into a 6 cm dish, and then cultured in an incubator for 24 hours. A solution of R2 liposome in PBS (phosphate buffered saline, D-PBS(−)) was adjusted to $2 \times 10^{-6}$ M and was added to the dish, and culturing was continued for 20 hours.
(3) The medium was removed, washing was performed twice with PBS (phosphate buffered saline, D-PBS(−)), and then 5 ml of a medium (5 ml of MEM Non-Essential Amino Acids Solution, 5 ml of antibiotic, 10 ml of 1M HEPES and 50 ml of FBS (fetal bovine serum) were added to 500 ml of Eagle's minimal essential medium) was added, and then the concentration of vitamin C in the media was adjusted to 12.8 mM by adding 0.55 ml of solution of vitamin C in PBS (phosphate buffered saline, D-PBS(−)).
(4) The luminescence was periodically observed with a fluorescence microscope (manufactured by Leica; IRB) and a CCD camera (manufactured by Leica; DFC350FX) (excitation light: 590-650 nm, monitoring wavelength: 664-734 nm) using a cut filter (manufactured by Leica; Y5) and the image was recorded.
(5) The obtained fluorescence microscope image was used to analyze the luminescence intensity time profile with image processing software (ImageJ).

[Experimental Results]

Figure 9:
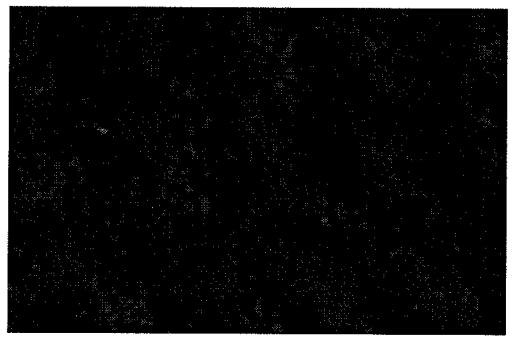
FIG. 9 is a pair of fluorescence microscope images taken after addition of R2 liposomes in a vitamin C bioimaging experiment using cells in Example 5, showing (A) luminescence in a cell line without addition of vitamin C (24 hours after R2 liposomes addition) and (B) luminescence in cell line with addition of vitamin C (240 min after vitamin C addition).
Figure 9:
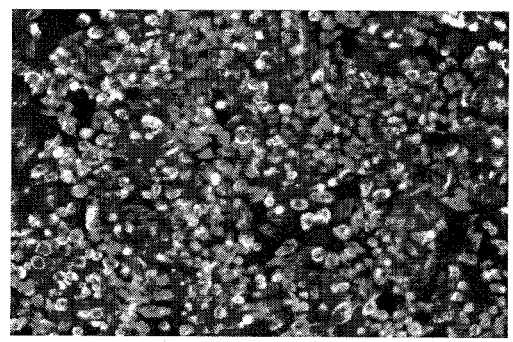
Figure 10:
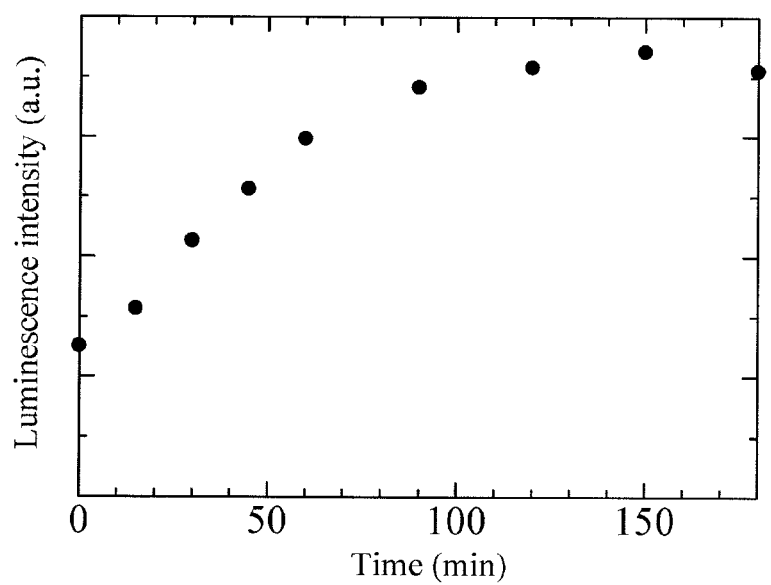
FIG. 10 is a graph showing the time-profile of luminescence intensity of intracellular R2 liposomes after vitamin C addition, obtained in a vitamin C bioimaging experiment with cells in Example 5.

A cell line without addition of vitamin C after adding R2 liposomes was observed in the same manner as above, but virtually no luminescence was seen even after 24 hours (FIG. 9A). In the vitamin C-added cell line, however, a significant change in the luminescence was seen after addition, with strong luminescence being confirmed even after 240 minutes (FIG. 9B). FIG. 10 shows the luminescence intensity time profile as analyzed using image processing software. This experiment demonstrated a reproducible exponential change in luminescence intensity, and successful bioimaging of vitamin C in cells. The rate of cellular uptake or intracellular reduction of a nitroxide radical(s) by vitamin C in vivo is reflected in the quantitative data of the intracellular luminescence intensity time profile based on image analysis, and this is expected to help elucidate the in vivo function of vitamin C.

Example 6

R2 Liposome and Hydrogen Peroxide Reactivity Experiment

Experiment Procedure (1) A solution of R2 liposome was prepared by steps (1)-(5) of the above Example 4.
(2) 1 M solution of hydrogen peroxide in PBS (phosphate buffered saline, D-PBS(−)) was prepared.
(3) The solution in the above (1) was diluted 10-folds with PBS (phosphate buffered saline, D-PBS(−)), and 1.5 ml of said diluted solution and a microstir bar were placed in a glass cell and stirred with a stirrer (1000 r.p.m).
(4) The stirred mixture was irradiated with a diode laser (manufactured by Yamaki; LDX-2615-650-TO3; wavelength: 650 nm) as excitation light, the luminescence was monitored at 695 nm using a spectrometer (manufactured by JASCO Co.; CT-25TP) and a photomultiplier (manufactured by Hamamatsu Photonics K.K.; R928), while adding 0.015 ml of solution of hydrogen peroxide in PBS (phosphate buffered saline, D-PBS(−)) obtained in the above (2), and the time-profile of luminescence intensity was measured. During this time, the angle and positional relationship were adjusted so that the optical fibers did not capture diffuse reflection from the microstir bar.
(5) As a control, the procedure in the above (4) was repeated using 8 mM solution of vitamin C in PBS (phosphate buffered saline, D-PBS(−)), instead of the solution of hydrogen peroxide in PBS (phosphate buffered saline, D-PBS(−)).

[Experimental Results]

Figure 11:
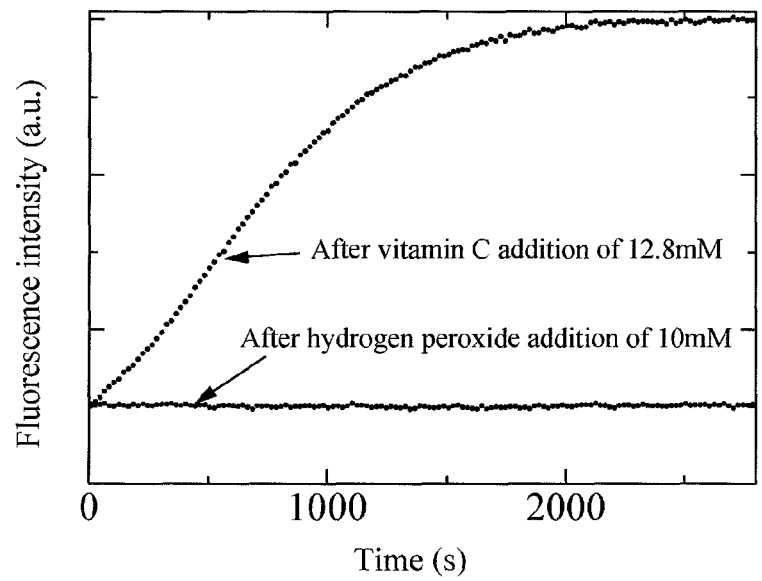
FIG. 11 is a graph showing the time-profile of luminescence intensity with reaction between R2 liposomes and hydrogen peroxide in Example 6.

This experiment was conducted to examine the effect of hydrogen peroxide, known to be a vitamin C by-product in the presence of the serum protein albumin, on the fluorogenic probes of the present invention. The 10 mM hydrogen peroxide solution added to the R2 liposomes in this experiment corresponds to 67 times the amount of hydrogen peroxide generated by 2 mM ascorbic acid in the presence of FBS. The luminescence intensity time profiles are shown in FIG. 11. The experiment demonstrated that hydrogen peroxide has no reactivity for the fluorogenic probes of the present invention. It was thus shown that reaction between the fluorogenic probes of the present invention and vitamin C is not affected by byproduct (hydrogen peroxide), or in other words, that the method of the present invention allows fluorescence bioimaging of vitamin C alone as a target.

Example 7

Real Time Observation of Intracellular Reduction of Dehydroascorbic Acid

Experiment Procedure (1) The R2 liposomes prepared by steps (1)-(5) in the above Example 4 were diluted 10-fold with DMF, the amount of the photosensitizer (complex R2) encapsulated into the liposomes was calculated from the absorbance of the absorption spectrum to determine the concentration, and the concentration was adjusted.
(2) HeLa cells ($2 \times 10^4$ cells/cm$^2$, purchased from Health Sciences Research Resources Bank) of 5 ml of medium were inoculated into a 6 cm dish, and then cultured in an incubator for 24 hours. A solution of R2 liposome in PBS (phosphate buffered saline, D-PBS(−)) was adjusted to $2 \times 10^{-6}$ M and was added to the dish, and culturing was continued for 20 hours.
(3) The medium was removed, washing was performed twice with PBS (phosphate buffered saline, D-PBS(−)), and then 5 ml of a medium (5 ml of MEM Non-Essential Amino Acids Solution, 5 ml of antibiotic, 10 ml of 1M HEPES and 50 ml of FBS (fetal bovine serum) were added to 500 ml of Eagle's minimal essential medium) was added, and then the concentration of dehydroascorbic acid in the media was adjusted to 12.8 mM by adding 0.55 ml of solution of dehydroascorbic acid in PBS (phosphate buffered saline, D-PBS(−)).
(4) The luminescence was periodically observed with a fluorescence microscope (excitation light: 590-650 nm, monitoring wavelength: 664-734 nm) using a cut filter (manufactured by Leica; Y5), and the image was recorded.

[Experimental Results]

Figure 12:
FIG. 12 is a pair of fluorescence microscope images taken after addition of dehydroascorbic acid in a real-time observation experiment of intracellular reduction of dehydroascorbic acid in Example 7, showing the luminescence in cell line (A) 2 minutes afterward and (B) 180 minutes afterward.
Figure 12:
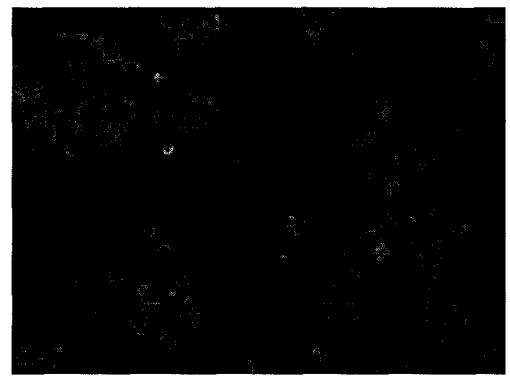

Dehydroascorbic acid is the oxidized form of vitamin C (ascorbic acid), and it is known to be rapidly reduced and converted to vitamin C when taken up into cells. This experiment was conducted to examine whether fluorescence bioimaging with a fluorogenic probe of the present invention allows real time observation of intracellular reduction of dehydroascorbic acid. FIG. 12(A) and FIG. 12(B) show fluorescence microscope images of cell lines 2 minutes and 180 minutes, respectively, after addition of dehydroascorbic acid. An increase in luminescence of the fluorogenic probe in the cells was observed after addition of dehydroascorbic acid (change occurred from FIG. 12(A) to FIG. 12(B)). Real time observation of intracellular reduction of dehydroascorbic acid was therefore successful. Also, quantitative analysis of the luminescence intensity time profiles based on image analysis, in the same manner as for vitamin C, is expected to allow determination of the intracellular uptake rate and intracellular reduction rate of dehydroascorbic acid.

INDUSTRIAL APPLICABILITY

The results described above demonstrate that (1) luminescence intensity increases after addition of vitamin C in liposome aqueous solution and methanol solution, (2) the reaction rate of a fluorogenic probe (complex) of the present invention is in a positive correlation with vitamin C concentration, and (3) the rate of increase in luminescence of a fluorogenic probe (complex) of the present invention matches the spin disappearance rate according to ESR. We therefore successfully developed a novel method of determining vitamin C in both hydrophilic and hydrophobic solvents.

Moreover, the present methods are superior to existing methods because (1) both excitation light and luminescence are observed in a range of high permeability to biological tissue (>650 nm), (2) luminescence is increased in aqueous liposome solutions which are biological membrane models, thus indicating potential for in vivo applications, (3) aqueous liposome solutions with complex R2, for example, exhibit a luminescence intensity increase ratio sufficient for fluorescence microscopy, with a maximum 500% increase, (4) in methanol, complex R1 exhibits an increase of about 150% and R2 an increase of about 6300%, which are high luminescence intensity ratios, (5) by replacing the TEMPO radical of R1 with PROXYL radical, which is known to have an even higher fluorescent quantum yield ratio than R0, an even higher luminescence intensity ratio is exhibited, while association effects can be eliminated by replacing the hydroxy group of the axial ligand with a trialkylsiloxy group, so that easy adjustment of luminescence intensity can be made by simple chemical modification which increases the luminescence intensity, (6) (phthalocyaninato)silicon complex encapsulated into liposomes (a liposome preparation of the invention) reaches the intracellular space and exhibits a reproducible consecutive reaction-type time profile for luminescence intensity, (7) since the liposome preparation of the invention is not affected by the various reducing substances in cells, specific detection and determination of vitamin C is possible, and (8) the reaction rate is slower than existing fluorogenic probes, so that it is suited for quantitation of pharmacological concentrations necessary for cancer treatment (0.3-20 mM) (confirmed at 0.4 mM-6.4 mM); therefore, the methods are expected to allow fluorescence bioimaging of vitamin C that has not been hitherto possible, for greater elucidation of the in vivo function of vitamin C.

The methods of the invention are therefore useful for detection and determination of vitamin C. In particular, the methods of the invention allow detection of vitamin C in vivo, which has not been possible to date, to potentially realize in vivo fluorescence bioimaging of vitamin C (in cells, for example) for research so that significant advances can be made in elucidating the in vivo function of vitamin C.

The invention claimed is:

1. A method for detection or determination of vitamin C in a sample, the method comprising the following steps:
   (1) contacting a redox-responsive fluorogenic probe consisting of a porphyrin or a phthalocyanine with a nitroxide radical(s) under irradiation with excitation light, with a sample;
   (2) monitoring the luminescence; and
   (3) optionally, determining the concentration of vitamin C in the sample based on the time-profile of luminescence intensity.

2. The method according to claim 1, wherein the porphyrin or the phthalocyanine with a nitroxide radical(s) is a compound of the following formula I:

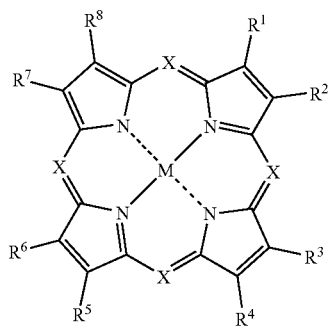

wherein
   X is N or CR', where R' is a hydrogen atom, a $C_{1-18}$ alkyl group, an aryl group or a nitrogen-containing heterocyclyl group;
   M is $H_2$ or an atom selected from elements of Groups 2-4 or Groups 8-15 of the Periodic Table;
   when M is an atom selected from elements of Groups 2-4 or Groups 8-15 of the Periodic Table, 1 or 2 axial ligands L may be present, where each L is independently a halogen atom, a hydroxyl group, a tri($C_{1-18}$ alkyl)silyloxy group or a nitroxide radical;

$R^1$, $R^2$, $R^3$, $R^4$, $R^5$, $R^6$, $R^7$ and $R^8$ are, independently of one another, a hydrogen atom, a $C_{1-18}$ alkyl group, a $C_{1-18}$ alkoxy group, an aryl group, a nitrogen-containing heterocyclyl group or a nitroxide radical, or $R^1$ and $R^2$ form an aromatic ring or a nitrogen-containing hetero ring together with the carbon atoms to which they are bonded, and the aromatic ring or the nitrogen-containing hetero ring is unsubstituted or substituted with one or more substituents selected from the group consisting of a halogen atom, a hydroxyl group, a sulfo group, a carboxyl group, a $C_{1-18}$ alkyl group, a $C_{1-18}$ alkoxy group, —$S(O)_{0-2}$—$C_{1-18}$ alkyl, —($OCH_2CH_2$)$_{1-8}$—O—$C_{1-6}$ alkyl, an aryl group and a nitrogen-containing heterocyclyl group, or may form a ring containing a nitroxide radical(s) together with two adjacent ring atoms of the aromatic ring or the nitrogen-containing hetero ring, $R^3$ and $R^4$ form an aromatic ring or nitrogen-containing hetero ring together with the carbon atoms to which they are bonded, and the aromatic ring or the nitrogen-containing hetero ring is unsubstituted or substituted with one or more substituents selected from the group consisting of a halogen atom, a hydroxyl group, a sulfo group, a carboxyl group, a $C_{1-18}$ alkyl group, a $C_{1-18}$ alkoxy group, —$S(O)_{0-2}$—$C_{1-18}$ alkyl, —($OCH_2CH_2$)$_{1-8}$—O—$C_{1-6}$ alkyl, an aryl group and a nitrogen-containing heterocyclyl group, or may form a ring containing a nitroxide radical(s) together with two adjacent ring atoms of the aromatic ring or the nitrogen-containing hetero ring, $R^5$ and $R^6$ form an aromatic ring or nitrogen-containing hetero ring together with the carbon atoms to which they are bonded, and the aromatic ring or the nitrogen-containing hetero ring is unsubstituted or substituted with one or more substituents selected from the group consisting of a halogen atom, a hydroxyl group, a sulfo group, a carboxyl group, a $C_{1-18}$ alkyl group, a $C_{1-18}$ alkoxy group, —$S(O)_{0-2}$—$C_{1-18}$ alkyl, —($OCH_2CH_2$)$_{1-8}$—O—$C_{1-6}$ alkyl, an aryl group and a nitrogen-containing heterocyclyl group, or may form a ring containing a nitroxide radical(s) together with two adjacent ring atoms of the aromatic ring or the nitrogen-containing hetero ring, or $R^7$ and $R^8$ form an aromatic ring or nitrogen-containing hetero ring together with the carbon atoms to which they are bonded, and the aromatic ring or the nitrogen-containing hetero ring is unsubstituted or substituted with one or more substituents selected from the group consisting of a halogen atom, a hydroxyl group, a sulfo group, a carboxyl group, a $C_{1-18}$ alkyl group, a $C_{1-18}$ alkoxy group, —$S(O)_{0-2}$—$C_{1-18}$ alkyl, —($OCH_2CH_2$)$_{1-8}$—O—$C_{1-6}$ alkyl, an aryl group and a nitrogen-containing heterocyclyl group, or may form a ring containing a nitroxide radical(s) together with two adjacent ring atoms of the aromatic ring or the nitrogen-containing hetero ring; with the proviso that at least one nitroxide radical is present in the compound.

3. The method according to claim 1, wherein the porphyrin or the phthalocyanine with a nitroxide radical(s) is a compound of the following formula II:

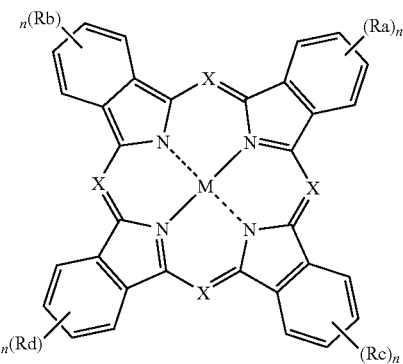

wherein
X is N or CR', where R' is a hydrogen atom, a $C_{1-18}$ alkyl group, an aryl group or a nitrogen-containing heterocyclyl group;

M is $H_2$ or an atom selected from elements of Groups 2-4 or Groups 8-15 of the Periodic Table;

when M is an atom selected from elements of Groups 2-4 or Groups 8-15 of the Periodic Table, 1 or 2 axial ligands L may be present, where each L is independently a halogen atom, a hydroxyl group, a tri($C_{1-18}$ alkyl)silyloxy group or a nitroxide radical;

each n is independently 0, 1, 2, 3 or 4; and

Ra, Rb, Rc and Rd are, independently of one another, a halogen atom, a hydroxyl group, a sulfo group, a carboxyl group, a $C_{1-18}$ alkyl group, a $C_{1-18}$ alkoxy group, —$S(O)_{0-2}$—$C_{1-18}$ alkyl, —$(OCH_2CH_2)_{1-8}$—O—$C_{1-6}$ alkyl, an aryl group or a nitrogen-containing heterocyclyl group, or when n is 2, two adjacent groups of each Ra, Rb, Rc and Rd may form a ring containing a nitroxide radical(s) together with ring atoms to which they are bonded;

with the proviso that at least one nitroxide radical is present in the compound.

4. The method according to claim 3, wherein M is an atom selected from elements of Group 2 or Groups 12-15 of the Periodic Table, and 1 or 2 axial ligands L are present.

5. The method according to claim 3, wherein the ring containing a nitroxide radical(s) formed together with ring atoms is 2,2,6,6-tetramethyl-1-piperidinyloxy (TEMPO) or 2,2,5,5-tetramethyl-1-pyrrolidinyloxy (PROXYL).

6. The method according to claim 1, wherein the porphyrin or the phthalocyanine with a nitroxide radical(s) is a complex of the following formula III:

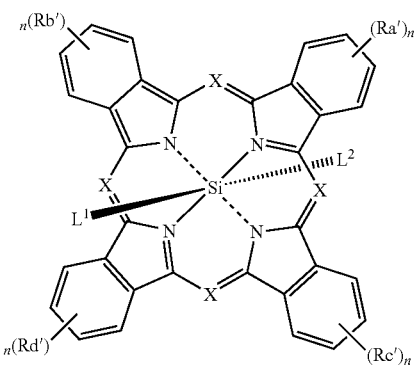

wherein
X is N or CR', where R' is a hydrogen atom, a $C_{1-18}$ alkyl group, an aryl group or a nitrogen-containing heterocyclyl group;

one of $L^1$ and $L^2$ is a nitroxide radical, and the other is a halogen atom, a hydroxyl group, a tri($C_{1-18}$ alkyl)silyloxy group or a nitroxide radical;

Ra', Rb', Rc' and Rd' are, independently of one another, a halogen atom, a hydroxyl group, a sulfo group, a carboxyl group, a $C_{1-18}$ alkyl group, a $C_{1-18}$ alkoxy group, —$S(O)_{0-2}$—$C_{1-18}$ alkyl, —$(OCH_2CH_2)_{1-8}$—O—$C_{1-6}$ alkyl, an aryl group or a nitrogen-containing heterocyclyl group; and each n is independently 0, 1, 2, 3 or 4.

7. The method according to claim 6, wherein X is N.

8. The method according to claim 6, wherein the nitroxide radical in $L^1$ or $L^2$ is of the following formula IV:

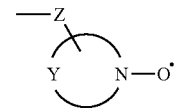

wherein
Y, together with N, forms a 5- to 6-membered, saturated or partially unsaturated, nitrogen-containing hetero ring, where the two atoms adjacent to the >N—O. group are tertiary carbon atoms, and the nitrogen-containing hetero ring optionally includes an additional N or O atom; and Z is a single bond or a spacer.

9. The method according to claim 8, wherein the nitroxide radical is a group comprising a 5- to 6-membered, saturated or partially unsaturated, nitrogen-containing hetero ring structure selected from 2,2,6,6-tetramethyl-1-piperidinyloxy (TEMPO), 2,2,5,5-tetramethyl-1-pyrrolidinyloxy (PROXYL), 4,4-dimethyl-3-oxazolidinyloxy (DOXYL) or nitronylnitroxide (NN).

10. The method according to claim 1, characterized in that the redox-responsive fluorogenic probe consisting of the porphyrin or the phthalocyanine with a nitroxide radical(s) is used in the form of a liposome preparation.

11. A method for detection of vitamin C in vivo, the method comprising the following steps:

(1) administering a redox-responsive fluorogenic probe consisting of a porphyrin or a phthalocyanine with a nitroxide radical(s) to a subject; and (2) irradiating the subject with excitation light having a wavelength of 650 nm or greater, and monitoring the luminescence.

12. The method according to claim 11, characterized in that the redox-responsive fluorogenic probe consisting of the porphyrin or the phthalocyanine with a nitroxide radical(s) is used in the form of a liposome preparation.

13. The method according to claim 12, wherein the porphyrin or the phthalocyanine with a nitroxide radical(s) is a compound of the following formula I:

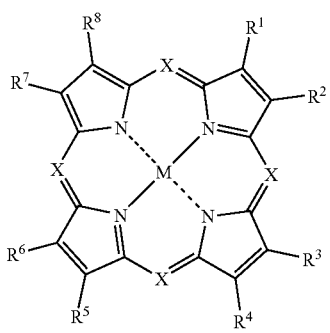

wherein
- X is N or CR', where R' is a hydrogen atom, a $C_{1-18}$ alkyl group, an aryl group or a nitrogen-containing heterocyclyl group;
- M is $H_2$ or an atom selected from elements of Groups 2-4 or Groups 8-15 of the Periodic Table;
- when M is an atom selected from elements of Groups 2-4 or Groups 8-15 of the Periodic Table, 1 or 2 axial ligands L may be present, where each L is independently a halogen atom, a hydroxyl group, a tri($C_{1-18}$ alkyl)silyloxy group or a nitroxide radical;
- $R^1$, $R^2$, $R^3$, $R^4$, $R^5$, $R^6$, $R^7$ and $R^8$ are, independently of one another, a hydrogen atom, a $C_{1-18}$ alkyl group, a $C_{1-18}$ alkoxy group, an aryl group, a nitrogen-containing heterocyclyl group or a nitroxide radical, or
- $R^1$ and $R^2$ form an aromatic ring or a nitrogen-containing hetero ring together with the carbon atoms to which they are bonded, and the aromatic ring or the nitrogen-containing hetero ring is unsubstituted or substituted with one or more substituents selected from the group consisting of a halogen atom, a hydroxyl group, a sulfo group, a carboxyl group, a $C_{1-18}$ alkyl group, a $C_{1-18}$ alkoxy group, —$S(O)_{0-2}$—$C_{1-18}$ alkyl, —($OCH_2CH_2)_{1-8}$—O—$C_{1-6}$ alkyl, an aryl group and a nitrogen-containing heterocyclyl group, or may form a ring containing a nitroxide radical(s) together with two adjacent ring atoms of the aromatic ring or the nitrogen-containing hetero ring,
- $R^3$ and $R^4$ form an aromatic ring or nitrogen-containing hetero ring together with the carbon atoms to which they are bonded, and the aromatic ring or the nitrogen-containing hetero ring is unsubstituted or substituted with one or more substituents selected from the group consisting of a halogen atom, a hydroxyl group, a sulfo group, a carboxyl group, a $C_{1-18}$ alkyl group, a $C_{1-18}$ alkoxy group, —$S(O)_{0-2}$—$C_{1-18}$ alkyl, —($OCH_2CH_2)_{1-8}$—O—$C_{1-6}$ alkyl, an aryl group and a nitrogen-containing heterocyclyl group, or may form a ring containing a nitroxide radical(s) together with two adjacent ring atoms of the aromatic ring or the nitrogen-containing hetero ring,
- $R^5$ and $R^6$ form an aromatic ring or nitrogen-containing hetero ring together with the carbon atoms to which they are bonded, and the aromatic ring or the nitrogen-containing hetero ring is unsubstituted or substituted with one or more substituents selected from the group consisting of a halogen atom, a hydroxyl group, a sulfo group, a carboxyl group, a $C_{1-18}$ alkyl group, a $C_{1-18}$ alkoxy group, —$S(O)_{0-2}$—$C_{1-18}$ alkyl, —($OCH_2CH_2)_{1-8}$—O—$C_{1-6}$ alkyl, an aryl group and a nitrogen-containing heterocyclyl group, or may form a ring containing a nitroxide radical(s) together with two adjacent ring atoms of the aromatic ring or the nitrogen-containing hetero ring, or
- $R^7$ and $R^8$ form an aromatic ring or nitrogen-containing hetero ring together with the carbon atoms to which they are bonded, and the aromatic ring or the nitrogen-containing hetero ring is unsubstituted or substituted with one or more substituents selected from the group consisting of a halogen atom, a hydroxyl group, a sulfo group, a carboxyl group, a $C_{1-18}$ alkyl group, a $C_{1-18}$ alkoxy group, —$S(O)_{0-2}$—$C_{1-18}$ alkyl, —($OCH_2CH_2)_{1-8}$—O—$C_{1-6}$ alkyl, an aryl group and a nitrogen-containing heterocyclyl group, or may form a ring containing a nitroxide radical(s) together with two adjacent ring atoms of the aromatic ring or the nitrogen-containing hetero ring; with the proviso that at least one nitroxide radical is present in the compound.

14. The method according to claim 12, wherein the porphyrin or the phthalocyanine with a nitroxide radical(s) is a compound of the following formula II:

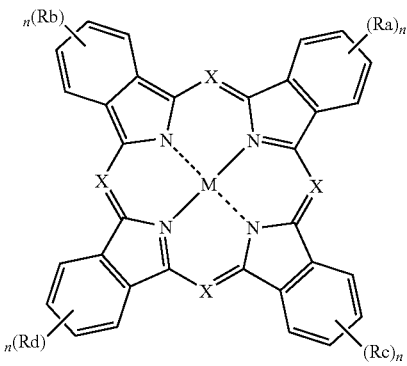

wherein
- X is N or CR', where R' is a hydrogen atom, a $C_{1-18}$ alkyl group, an aryl group or a nitrogen-containing heterocyclyl group;
- M is $H_2$ or an atom selected from elements of Groups 2-4 or Groups 8-15 of the Periodic Table;
- when M is an atom selected from elements of Groups 2-4 or Groups 8-15 of the Periodic Table, 1 or 2 axial ligands L may be present, where each L is independently a halogen atom, a hydroxyl group, a tri($C_{1-18}$ alkyl)silyloxy group or a nitroxide radical;
- each n is independently 0, 1, 2, 3 or 4; and
- Ra, Rb, Rc and Rd are, independently of one another, a halogen atom, a hydroxyl group, a sulfo group, a carboxyl group, a $C_{1-18}$ alkyl group, a $C_{1-18}$ alkoxy group, —$S(O)_{0-2}$—$C_{1-18}$ alkyl, —($OCH_2CH_2)_{1-8}$—O—$C_{1-6}$ alkyl, an aryl group or a nitrogen-containing heterocyclyl group, or when n is 2, two adjacent groups of each Ra, Rb, Rc and Rd may form a ring containing a nitroxide radical(s) together with ring atoms to which they are bonded;

with the proviso that at least one nitroxide radical is present in the compound.

15. The method according to claim 14, wherein M is an atom selected from elements of Group 2 or Groups 12-15 of the Periodic Table, and 1 or 2 axial ligands L are present.

16. The method according to claim 14, wherein the ring containing a nitroxide radical(s) formed together with the ring atoms is 2,2,6,6-tetramethyl-1-piperidinyloxy (TEMPO) or 2,2,5,5-tetramethyl-1-pyrrolidinyloxy (PROXYL).

17. The method according to claim 12, wherein the porphyrin or the phthalocyanine with a nitroxide radical(s) is a complex of the following formula III:

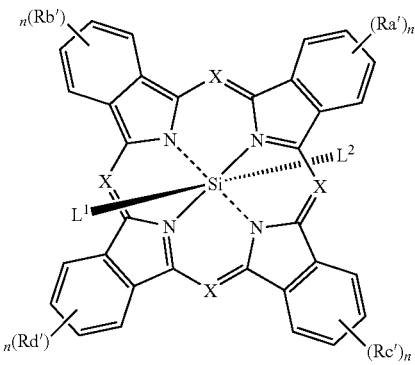

wherein

X is N or CR', where R' is a hydrogen atom, a $C_{1-18}$ alkyl group, an aryl group or a nitrogen-containing heterocyclyl group;

one of $L^1$ and $L^2$ is a nitroxide radical, and the other is a halogen atom, a hydroxyl group, a tri($C_{1-18}$ alkyl)silyloxy group or a nitroxide radical;

Ra', Rb', Rc' and Rd' are, independently of one another, a halogen atom, a hydroxyl group, a sulfo group, a carboxyl group, a $C_{1-18}$ alkyl group, a $C_{1-18}$ alkoxy group, —S(O)$_{0-2}$—C$_{1-18}$ alkyl, —(OCH$_2$CH$_2$)$_{1-8}$—O—C$_{1-6}$ alkyl, an aryl group or a nitrogen-containing heterocyclyl group; and each n is independently 0, 1, 2, 3 or 4.

18. The method according to claim 17, wherein X is N.

19. The method according to claim 17, wherein the nitroxide radical in $L^1$ or $L^2$ is of the following formula IV:

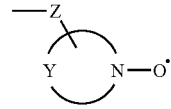

wherein

Y, together with N, forms a 5- to 6-membered, saturated or partially unsaturated, nitrogen-containing hetero ring, where the two atoms adjacent to the >N—O. group are tertiary carbon atoms, and the nitrogen-containing hetero ring optionally includes an additional N or O atom; and Z is a single bond or a spacer.

20. The method according to claim 19, wherein the nitroxide radical is a group comprising a 5- to 6-membered, saturated or partially unsaturated, nitrogen-containing hetero ring structure selected from 2,2,6,6-tetramethyl-1-piperidinyloxy (TEMPO), 2,2,5,5-tetramethyl-1-pyrrolidinyloxy (PROXYL), 4,4-dimethyl-3-oxazolidinyloxy (DOXYL) or nitronylnitroxide (NN).

* * * * *